United States Patent
Hori et al.

(10) Patent No.: US 9,492,248 B2
(45) Date of Patent: Nov. 15, 2016

(54) DENTAL IMPLANT

(75) Inventors: Koji Hori, Kyoto (JP); Masayoshi Nishizawa, Kyoto (JP); Ariyoshi Matsuno, Kyoto (JP); Ryuichi Yoshimoto, Kyoto (JP)

(73) Assignee: SHOFU INC., Kyoto (JP)

( * ) Notice: Subject to any disclaimer, the term of this patent is extended or adjusted under 35 U.S.C. 154(b) by 88 days.

(21) Appl. No.: 13/544,346

(22) Filed: Jul. 9, 2012

(65) Prior Publication Data

US 2013/0177874 A1    Jul. 11, 2013

(30) Foreign Application Priority Data

Aug. 2, 2011   (JP) ................. 2011-169228

(51) Int. Cl.
*A61C 8/00*   (2006.01)
(52) U.S. Cl.
CPC ........... *A61C 8/0025* (2013.01); *A61C 8/0024* (2013.01); *A61C 8/0068* (2013.01); *A61C 8/0069* (2013.01); *A61C 8/0075* (2013.01)
(58) Field of Classification Search
CPC ............... A61C 8/0028; A61C 8/0024; A61C 8/0025; A61C 8/0069; A61C 8/0075; A61C 8/0068
USPC ...................... 433/172–176, 201.1
See application file for complete search history.

(56) References Cited

U.S. PATENT DOCUMENTS

| | | | |
|---|---|---|---|
| 6,547,564 B1 | 4/2003 | Hansson | |
| 7,677,891 B2 * | 3/2010 | Niznick | 433/174 |
| 2004/0006346 A1 * | 1/2004 | Holmen et al. | 606/73 |
| 2004/0219488 A1 * | 11/2004 | Choi et al. | 433/173 |
| 2008/0014556 A1 * | 1/2008 | Neumeyer | 433/174 |
| 2008/0261175 A1 * | 10/2008 | Hurson | 433/173 |
| 2009/0155743 A1 | 6/2009 | Garcia Saban et al. | |
| 2011/0045437 A1 * | 2/2011 | Arni | 433/174 |
| 2012/0178048 A1 * | 7/2012 | Cottrell | 433/174 |

FOREIGN PATENT DOCUMENTS

| | | |
|---|---|---|
| JP | 2002-520119 | 7/2002 |
| JP | 4282479 | 3/2009 |
| JP | 4278305 | 6/2009 |
| JP | 2010-524606 | 7/2010 |
| JP | 2010-524607 | 7/2010 |
| WO | 2007/091997 | 8/2007 |

(Continued)

*Primary Examiner* — Heidi M Eide
(74) *Attorney, Agent, or Firm* — Hamre, Schumann, Mueller & Larson, P.C.

(57) ABSTRACT

A dental implant includes a male threading part and an implantation torque increasing part from the tip side. The male threading part includes multiple threading parts that have the same lead but different pitches, with the pitch increasing toward the tip side. The outer diameter of the male threading part is constant or increases toward the implantation torque increasing part. The implantation torque increasing part includes thread crests that have a different lead from the lead of the male threading part or a projecting row that is continuous circumferentially. In cross-section, a contour line connecting tops of the thread crests of the threading part that is adjacent to the implantation torque increasing part is a straight line, and the tops of the thread crests or the top of the projecting row of the implantation torque increasing part are located on an extension line of the contour line.

15 Claims, 21 Drawing Sheets

(56) References Cited

FOREIGN PATENT DOCUMENTS

| WO | 2008/128756 | | 10/2008 | |
|---|---|---|---|---|
| WO | WO2009/154336 A1 | * | 12/2009 | ............... A61C 8/00 |
| WO | WO 2011/062976 | * | 5/2011 | ........... A61C 13/093 |

* cited by examiner

DENTAL IMPLANT

BACKGROUND OF THE INVENTION

1. Field of the Invention

The present invention relates to a dental implant that can be clinically applied in a simple and versatile manner with the jawbone serving as the anchor.

2. Description of the Related Art

As the general practice for dental implants that use the jawbone as the anchor, a hole (bone hole) with a diameter that is substantially the same as or slightly smaller than the outer diameter of a dental implant is formed in the jawbone using an implant drill, and then the dental implant is hammered or screwed into the bone hole so as to implant it. Thus the dental implant is implanted at a desired jawbone location.

Known examples of dental implants include the following: a two-piece type of dental implant that is constituted by two parts, namely a fixture serving as the dental root replacement and an abutment serving as the dental crown anchor replacement, with the abutment being joined to the fixture; a three-piece type of dental implant that is constituted by three parts, namely a fixture, an abutment, and a screw, with the abutment being fixed to the fixture using the screw; and a one-piece type of dental implant in which the fixture and the abutment are integrated.

Examples of dental implant procedures include the following: a two-part procedure in which the dental implant is implanted and the gum tissue is sutured such that the dental implant is not exposed inside the oral cavity, and then a healing period is allowed before a prosthesis (dental crown) is attached; and a one-part procedure in which the surrounding gum tissue is sutured so as to leave the implanted dental implant exposed.

The one-piece type of dental implant uses the simplest procedure and is advantageous in terms of physical strength as well. Also, the one-part procedure, in which the entire treatment is completed at one time by implanting the dental implant and attaching the occlusion site prosthesis serving as the upper structure immediately thereafter, is advantageous in terms of being able to shorten the total amount of time or number of days for the procedure and being able to reduce the financial and mental burden borne by the staff and patient. However, the one-piece type of dental implant and the one-part procedure only can be applied when conditions in the oral cavity are met, such as the condition that the bone material and bone mass of the jawbone are sufficient, the condition that the oral hygiene condition is favorable, and the condition that the procedure site and tooth alignment are such that the procedure site is not subjected to high occlusal pressure. The dental implant type and procedure have therefore been appropriately selected case-by-case.

Although recent years have seen advances in the development of technology for making dental implants easier to use, and products with improved surface texture, shape, and the like are being launched, these products all have advantages and disadvantages.

Japanese Patent No. 4278305 discloses a dental implant that can be easily implanted into a bone tissue structure. Formed on the outer face of this dental implant are two types of male threading that have the same or substantially the same lead (the amount of travel in the axial direction when turned one time, which is described as "pitch" in Japanese Patent No. 4278305) and different pitches (the distance between adjacent thread crests, which is described as "inter-crest interval" in Japanese Patent No. 4278305). The dental implant of Japanese Patent No. 4278305 is intended to only facilitate implantation in a bone tissue structure, and does not give consideration to the accurate implantation of a dental implant at the location determined at the time of diagnosis.

Japanese Patent No. 4282479 is a patent held by the same person as the above-described Japanese Patent No. 4278305 and discloses a dental implant in which the portion that engages with the cortical bone tissue layer has a tapered shape such that the diameter increases toward the upper side. Japanese Patent No. 4282479 discloses that when this dental implant is screwed into the jawbone, an increase in torque can be recognized in a sensory manner with the tapered portion, thus enabling accurate implanting of the dental implant at the location determined at the time of diagnosis.

However, with the tapered portion in Japanese Patent No. 4282479 as well, the male threading is formed so as to continuously have the same lead and same pitch from the portion more toward the tip side. Accordingly, the amount of increase in the torque is constant when screwing in the tapered portion. Therefore, in reality, it is difficult to accurately implant the dental implant at the location determined at the time of diagnosis.

It has been confirmed that in many cases after the implantation of a dental implant, approximately 1 mm of bone resorption (regression) occurs from the bone surface toward the interior of the bone. One cause of this bone resorption is that bacteria intrudes from the bone surface side into the border between the bone and the dental implant, and the bone is eroded toward the interior of the bone along the border between the bone and the dental implant. According to reviews carried out by the inventors of the present invention, when microscopically viewed, this bone erosion does not advance in parallel toward the central axis of the dental implant, but rather advances along the roots of for example, the male threading formed on the outer surface of the dental implant. With the dental implant of Japanese Patent No. 4282479, the male threading is formed so as to continuously have the same lead and same pitch in the tapered portion and the portion farther toward the tip side, and therefore there is the problem that bone resorption caused by bacteria readily progresses along the roots of the male threading.

SUMMARY OF THE INVENTION

A first object of the present invention is to provide a dental implant that can be accurately implanted at a location determined at the time of diagnosis. A second object of the present invention is to provide a dental implant that can reduce bone resorption (regression) in the vicinity of the bone surface.

A dental implant according to the present invention is a dental implant for implantation in a jawbone, including: a male threading part and an implantation torque increasing part on an outer face of the dental implant in the stated order from the tip side along the direction of a central axis of the dental implant, the male threading part and the implantation torque increasing part being coaxial with the central axis. The male threading part includes a plurality of threading parts that have the same lead and different pitches. The plurality of threading parts are arranged in order of pitch magnitude such that the pitch increases toward the tip side. The outer diameter of the male threading part is constant in the central axis direction or increases toward the implantation torque increasing part. The implantation torque increasing part includes thread crests that have a different lead from the lead of the male threading part or a projecting row that is continuous in the circumferential direction. In a cross-section that includes the central axis, a contour line that connects the tops of thread crests of among the plurality of threading parts, the threading part that is adjacent to the implantation torque increasing part in order along the central axis direction is a straight line, and the tops of the thread crests or the top of the projecting row of the implantation torque increasing part are located on an extension line of the contour line.

DETAILED DESCRIPTION OF THE INVENTION

Figure 1A:
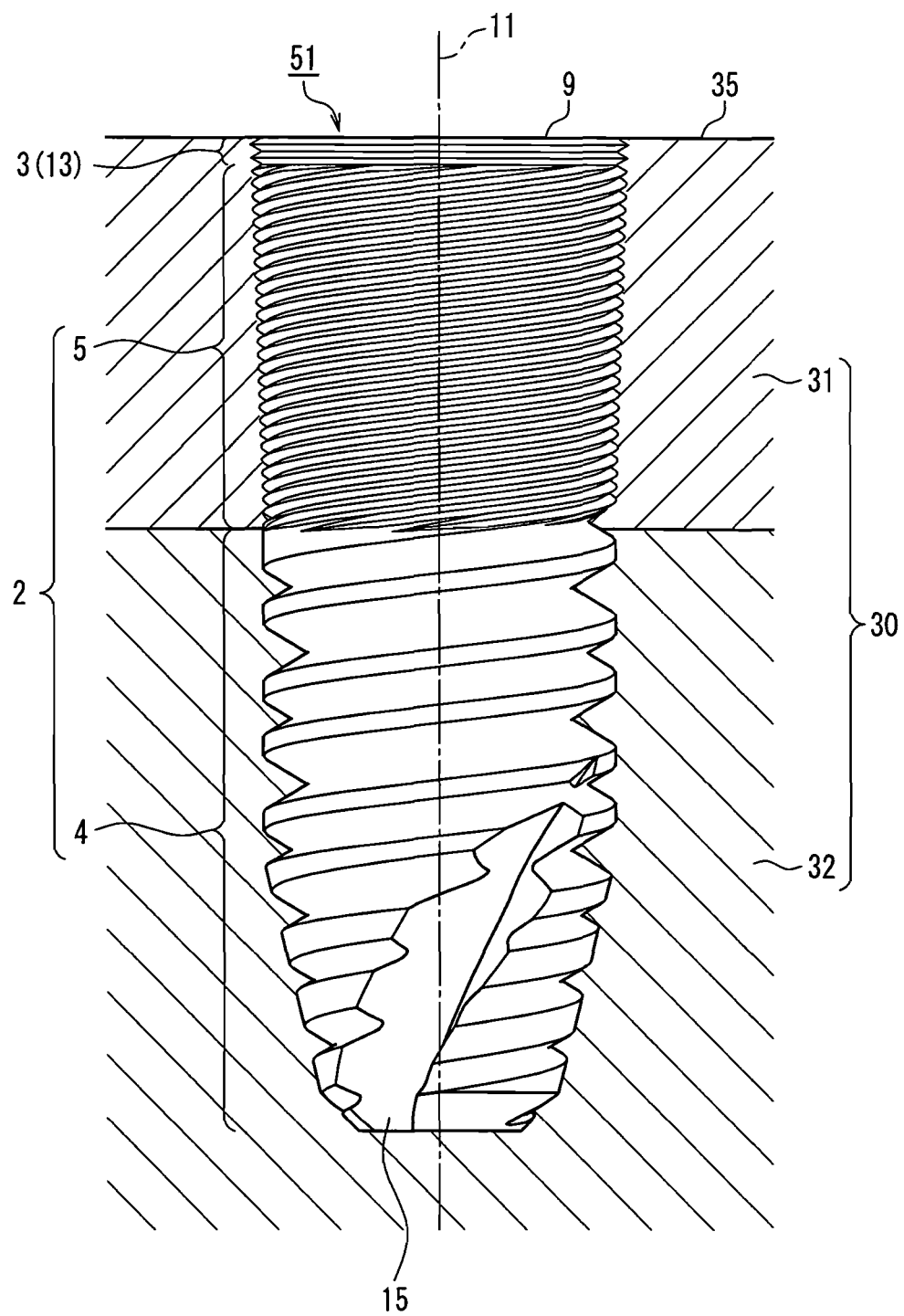
FIG. 1A is a side view of a dental implant according to Embodiment 1 of the present invention in the state of being implanted in a jawbone.

A dental implant according to the present invention is a dental implant for implantation in a jawbone, including: a male threading part and an implantation torque increasing part on an outer face of the dental implant in the stated order from the tip side along the direction of a central axis of the dental implant, the male threading part and the implantation torque increasing part being coaxial with the central axis. The male threading part includes a plurality of threading parts that have the same lead and different pitches. The plurality of threading parts are arranged in order of pitch magnitude such that the pitch increases toward the tip side. The outer diameter of the male threading part is constant in the central axis direction or increases toward the implantation torque increasing part. The implantation torque increasing part includes thread crests that have a different lead from the lead of the male threading part or a projecting row that is continuous in the circumferential direction. In a cross-section that includes the central axis, a contour line that connects the tops of thread crests of among the plurality of threading parts, the threading part that is adjacent to the implantation torque increasing part in order along the central axis direction is a straight line, and the tops of the thread crests or the top of the projecting row of the implantation torque increasing part are located on an extension line of the contour line.

According to the present invention, the implantation torque non-continuously (sharply) increases when the implantation torque increasing part starts to come into contact with and be implanted into the jawbone. Since the practitioner can recognize this increase in torque in a sensory manner, the dental implant can be accurately implanted at the implantation location determined at the time of diagnosis.

Also, appropriately setting the configuration of the implantation torque increasing part enables bone resorption (regression) in the vicinity of the bone surface to be reduced.

The above-described effects can be obtained regardless of the dental implant specifications.

In the above dental implant of the present invention, the implantation torque increasing part may be made up of a plurality of projecting rows that are continuous in the circumferential direction. This configuration enables further reducing of the bone resorption (regression) that occurs due to the intrusion of bacteria from the bone surface into the border between the bone and the dental implant, thus raising the possibility of also being able to prevent the occurrence of bone resorption (regression).

Alternatively, the implantation torque increasing part may be made up of minute male threading that is provided with thread crests whose lead is lower than the lead of the male threading part. As another alternative, the implantation torque increasing part may be made up of a single projecting row that is continuous in the circumferential direction.

It is preferable that the implantation torque increasing part is configured such that an implantation torque required to implant the implantation torque increasing part into the jawbone is greater than an implantation torque required to implant, among the plurality of threading parts, the threading part that is adjacent to the implantation torque increasing part into the jawbone. This enables the dental implant to be more accurately implanted at the implantation location determined at the time of diagnosis.

It is preferable that the length, with respect to the central axis direction, of an area of the male threading part in which the tops of the thread crests are located on the contour line and the extension line thereof is greater than or equal to 2.0 mm, or more preferably in the range of 3.2 mm to 4.0 mm inclusive.

It is preferable that the length of the implantation torque increasing part in the central axis direction is in the range of 0.1 mm to 10 mm inclusive, or more preferably in the range of 0.2 mm to 0.5 mm inclusive.

It is preferable that an angle that the contour line forms with the central axis is in the range of 0.5 degrees to 8 degrees inclusive, or more preferably in the range of 1 degree to 4 degrees inclusive.

It is preferable that the length of the lead that is common to the plurality of threading parts in the central axis direction is in the range of 0.5 mm to 2.4 mm inclusive, or more preferably in the range of 0.8 mm to 1.5 mm inclusive.

It is preferable that the pitches of the plurality of threading parts are expressed by an integer ratio.

It is preferable that the threading part that is arranged most toward the tip side among the plurality of threading parts has multiple-start thread.

It is preferable that a tip portion of the male threading part is formed on a tapered face whose cone angle is greater than that of another portion of the male threading part.

It is preferable that the dental implant includes a tap groove having a self tapping function at the tip or the vicinity thereof.

Hereinafter, the present invention will be described in detail by way of preferred embodiments. It should be noted that the present invention is not intended to be limited to the following embodiments. Also, for the sake of convenience in the description, the drawings that are referenced in the following description show simplifications of among the constituent members of the embodiment of the present invention, only relevant members that are necessary for describing the present invention. The present invention can therefore include arbitrary constituent members that are not shown in the following drawings. Furthermore, regarding the dimensions of the members in the drawings, the dimensions of the actual constituent members, the ratios of the dimensions of the members, and the like are not shown faithfully.

Embodiment 1

Figure 1B:
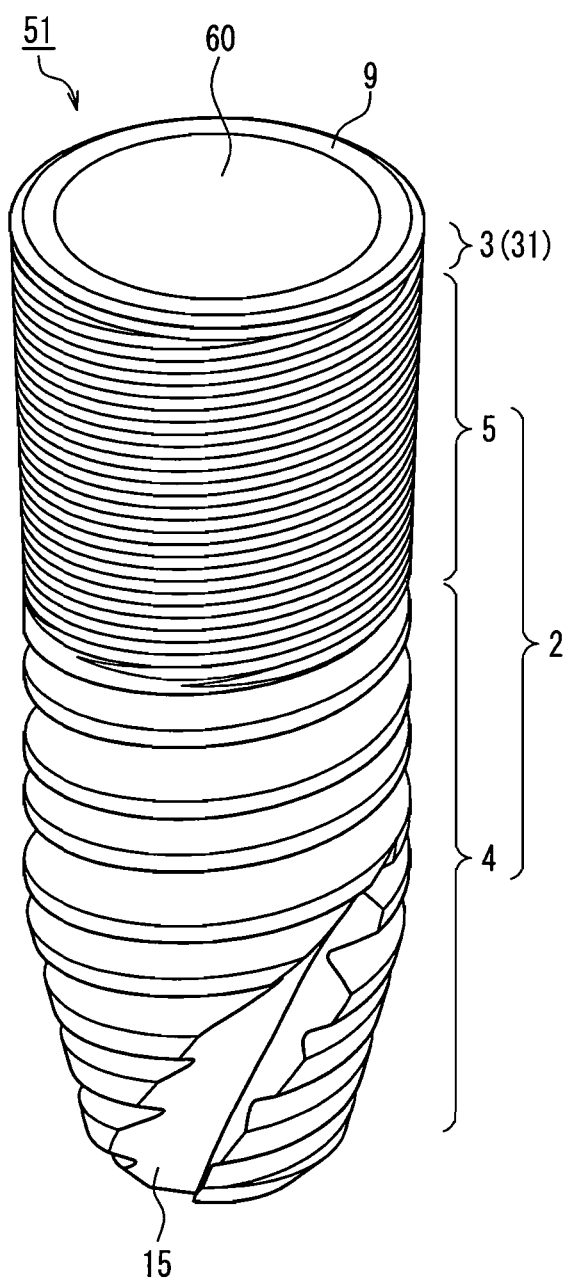
FIG. 1B is a perspective view of the dental implant according to Embodiment 1 of the present invention shown in FIG. 1A as viewed from above.
Figure 1C:
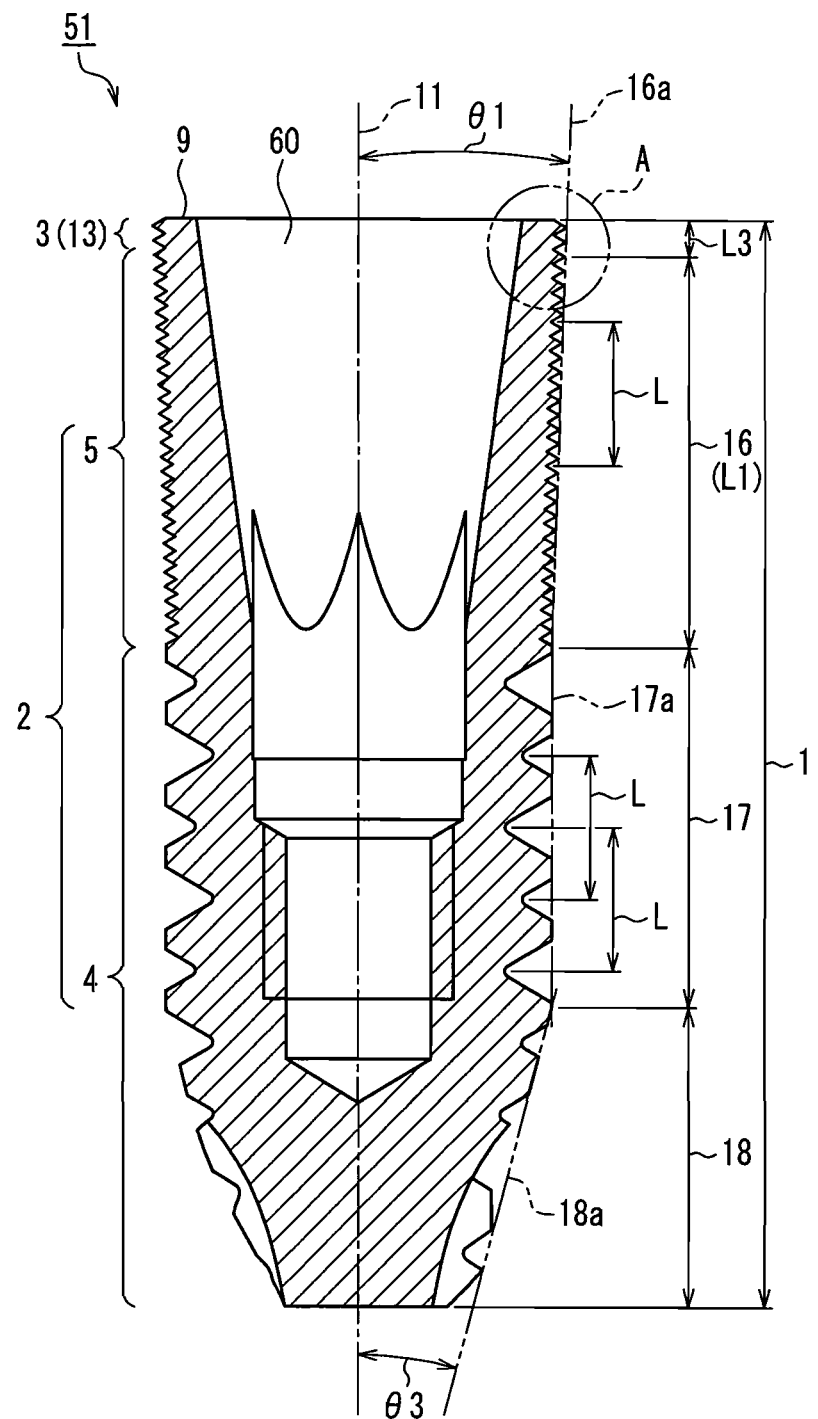
FIG. 1C is a cross-sectional side view of the dental implant according to Embodiment 1 of the present invention shown in FIG. 1A.
Figure 1D:
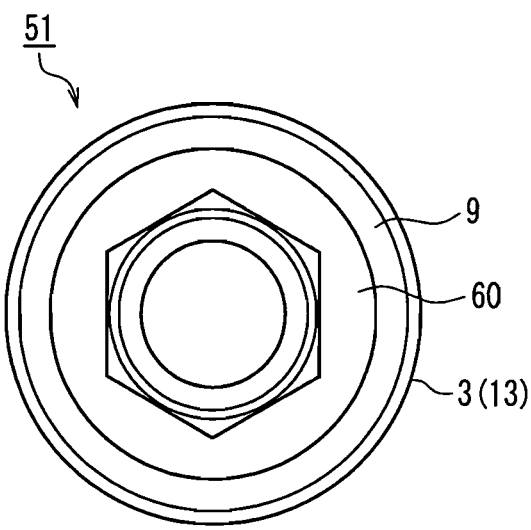
FIG. 1D is a plan view of the dental implant according to Embodiment 1 of the present invention shown in FIG. 1A as viewed from above.
Figure 1E:
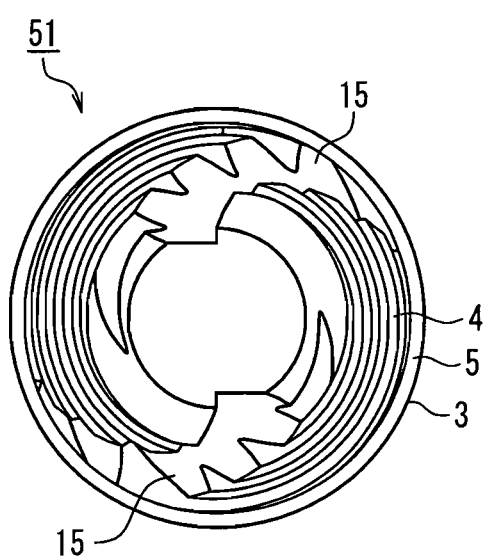
FIG. 1E is a bottom view of the dental implant according to Embodiment 1 of the present invention shown in FIG. 1A as viewed from below.
Figure 1F:
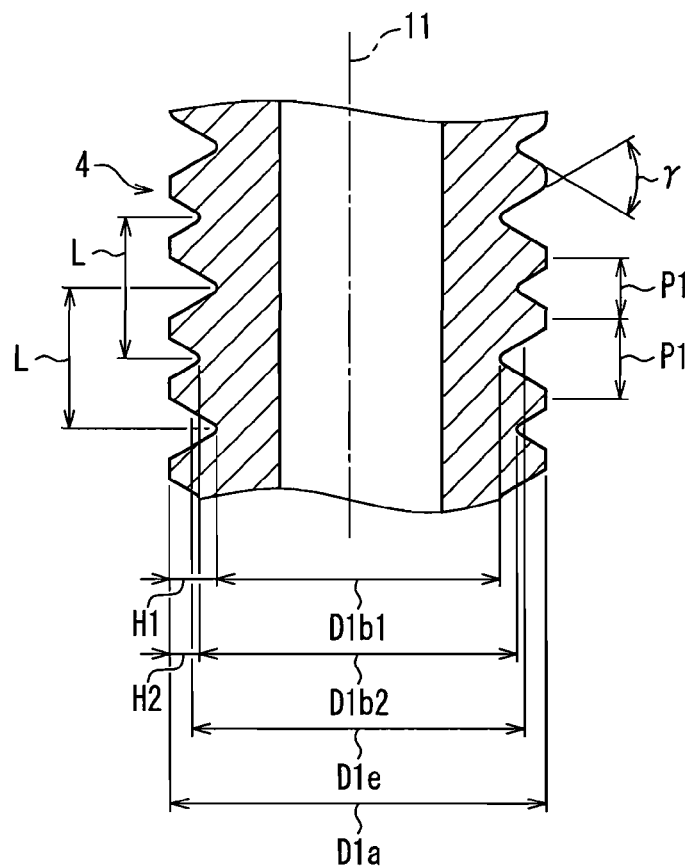
FIG. 1F is a partial enlarged cross-sectional side view of a first threading part of the dental implant according to Embodiment 1 of the present invention shown in FIG. 1A.
Figure 1G:
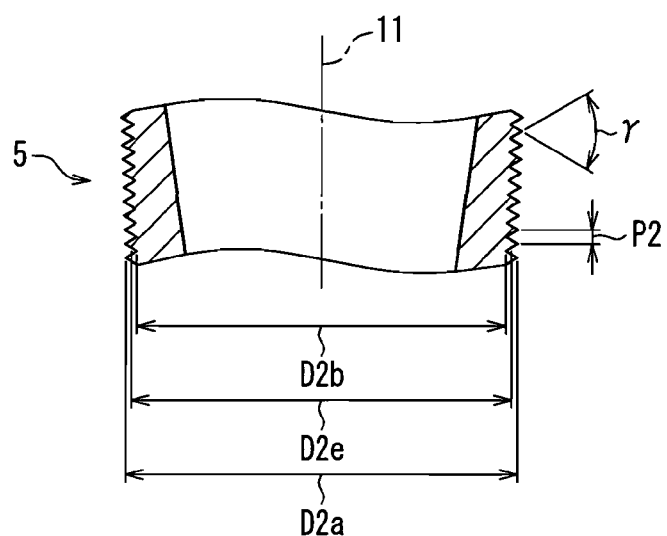
FIG. 1G is a partial enlarged cross-sectional side view of a second threading part of the dental implant according to Embodiment 1 of the present invention shown in FIG. 1A.

FIG. 1A is a side view of a dental implant 51 according to Embodiment 1 of the present invention in the state of being implanted in a jawbone 30. This dental implant 51 can be used as a two-piece or three-piece dental implant, and only the fixture thereof is shown in FIG. 1A. Also, this dental implant 51 can be applied to both the one-part procedure and the two-part procedure. A dashed-dotted line 11 indicates the central axis (main axis) along the longitudinal direction of the dental implant 51. Gum tissue that covers a bone surface 35 of the jawbone 30 is not shown in FIG. 1A. For the sake of convenience in the following description, with respect to the central axis 11 direction of the dental implant 51, the side on which the dental crown is attached (the upper side with respect to the paper plane of FIG. 1A) is referred to as the "dental crown side" or the "upper side", and the side toward which the dental implant is implanted into the jawbone 30 (the lower side with respect to the paper plane of FIG. 1A) is referred to as the "tip side" or the "lower side". FIG. 1B is a perspective view of the dental implant 51 as viewed from above, FIG. 1C is a cross-sectional side view of the dental implant 51 taken along a plane that includes the central axis 11, FIG. 1D is a plan view of the dental implant 51 as viewed from above, and FIG. 1E is a bottom view of the dental implant 51 as viewed from below. FIG. 1F is a partial enlarged cross-sectional side view of a first threading part 4 of the dental implant 51, and FIG. 1G is a partial enlarged cross-sectional side view of a second threading part 5 of the dental implant 51.

A male threading part 2 and an implantation torque increasing part 3 are formed on the outer face of the dental implant 51 of the present embodiment in the stated order from the tip side toward the dental crown side along the central axis 11 direction.

The male threading part 2 is constituted by the first threading part 4 on the tip side and the second threading part 5 on the dental crown side. Male threading that is coaxial with the central axis 11 of the dental implant 51 is formed on both the first threading part 4 and the second threading part 5. The male threading of the first threading part 4 has the same lead L as the male threading of the second threading part 5, but a higher pitch. Here, "lead" refers to the amount of travel in the central axis 11 direction when the male threading is rotated one time, and "pitch" refers to the pitch (period) of adjacent thread crests in the central axis 11 direction. In this example, the first threading part 4 is provided with double-start thread made up of two spiral grooves that have the same crest diameter $D1a$ and different root diameters $D1b1$ and $D1b2$ as shown in FIG. 1F, and the second threading part 5 is provided with multiple-start thread made up of three or more spiral grooves that have the same crest diameter $D2a$ and also the same root diameter $D2b$ as shown in FIG. 1G.

The implantation torque increasing part 3 is constituted by multiple projecting rows 13 that are coaxial with the central axis 11 of the dental implant 51. The projecting rows are annular projections (ribs or ridges) that are continuous in the circumferential direction of the dental implant 51. Grooves (or recessions) that are continuous in the circumferential direction of the dental implant 51 are formed between projecting rows that are adjacent in the central axis 11 direction. It is preferable that the pitch of the projecting rows 13 is lower than the pitch of the second threading part 5 that is adjacent to the projecting rows 13. Here, the pitch of the projecting rows 13 refers to the pitch (period) of projecting rows (or grooves) that are adjacent in the central axis 11 direction.

The first threading part 4 and the second threading part 5 that constitute the male threading part 2 have the same winding direction. Here, the "winding direction" of the threading refers to the direction of rotation of the threading that is necessary in order to move the threading in the direction of moving away when viewing the threading along the axis thereof.

In the cross-sectional view of the dental implant 51 taken along a plane that includes the central axis 11 as shown in FIG. 1C, the outer form (contour shape) of the dental implant 51 is defined by the "contour line". The "contour line" is defined as the line that connects the tops of the thread crests formed in the male threading part 2 (the places farthest away from the central axis 11) in order along the central axis 11 direction. In this example, the male threading part 2 can be divided into three regions, namely a first region 16, a second region 17, and a third region 18, in the stated order from the dental crown side to the tip side, according to the slope of the contour line (i.e., the angle that the contour line forms with the central axis 11).

The first region 16 corresponds to the region in which the second threading part 5 is formed. The contour line of the first region 16 (hereinafter referred to as the "first contour line 16a") is a straight line, and is tilted at an angle θ1 with respect to the central axis 11 such that the distance to the central axis 11 decreases with movement toward the tip side of the dental implant 51. The tops of the projecting rows among the projecting rows 13 that constitute the implantation torque increasing part 3 are located on an extension line extending upward from the first contour line 16a (see later-described FIG. 2A). In other words, the second threading part 5 in the first region 16 and the adjacent implantation torque increasing part 3 are formed on a common tapered face (conical face), and the first contour line 16a corresponds to the generatrix of this tapered face (conical face).

The second region 17 includes a portion of the first threading part 4 on the second threading part 5 side. The contour line of the second region 17 (hereinafter referred to as the "second contour line 17a") is a straight line, and is parallel with the central axis 11. In other words, the portion of the first threading part 4 on the second threading part 5 side in the second region 17 is formed on a common cylindrical face, and the second contour line 17a corresponds to the generatrix of this cylindrical face.

The third region 18 includes a portion of the first threading part 4 on the tip side. The contour line of the third region 18 (hereinafter referred to as the "third contour line 18a") is a straight line, and is tilted at an angle θ3 with respect to the central axis 11 such that the distance to the central axis 11 decreases with movement toward the tip side of the dental implant 51. The angle θ3 is greater than the angle θ1 (θ3>θ1). In other words, the portion of the first threading part 4 on the tip side in the third region 18 is formed on a common tapered face (conical face), and the third contour line 18a corresponds to the generatrix of the tapered face (conical face). The cone angle of the tapered face of the third region 18 is greater than the cone angle of the tapered face of the first region 16.

A portion 1 (hereinafter referred to as the "implantation portion 1") from the tip of the dental implant 51 to a dental crown-side end (generally called the "bone end") 9 of the implantation torque increasing part 3 (see FIG. 1C) is implanted into the jawbone 30 by being brought into contact with and engaged with the jawbone 30 as shown in FIG. 1A. Accordingly, it is desirable that the implantation portion 1 achieves favorable osseointegration with the jawbone.

The jawbone 30 is constituted by high-density, hard cortical bone 31 on the surface side and low-density, soft cancellous bone 32 inward of the cortical bone 31. The average thickness of the cortical bone 31 is 2 to 3 mm. It is anticipated that in many cases after the implantation of a dental implant, approximately 1 mm of bone resorption (regression) occurs from the bone surface toward the interior of the bone. It should be noted that these are ordinary average numerical values, and there are various optimum shapes for the dental implant depending on the case and the procedure.

The dental implant 51 is designed such that the implantation torque increasing part 3 and the first region 16 engage with the cortical bone 31, and the second region 17 and the third region 18 engage with the cancellous bone 32.

Since the second threading part 5 that constitutes the first region 16 corresponds to the hard cortical bone 31, it is preferable that, as shown in FIG. 1G, a threading pitch P2 of the second threading part 5 is reduced, and the root diameter D2b of the male threading is increased, that is to say, an effective diameter D2e is increased. This enables implanting the second threading part 5 into the cortical bone 31 without requiring excessive implantation torque, and enables realizing physical fixing of the dental implant 51 at the beginning of implantation.

It is desirable that a length L1 (see FIG. 1C) of the first region 16 (the second threading part 5 in Embodiment 1) in the central axis 11 direction is selected according to the thickness of the cortical bone 31, and generally it is preferable that the lower limit of the length L1 is greater than or equal to 2.0 mm, or more preferably greater than or equal to 3.2 mm. Also, it is preferable that the upper limit of the length L1 is less than or equal to 4.0 mm.

On the other hand, since the first threading part 4 that constitutes the second region 17 and the third region 18 corresponds to the soft cancellous bone 32, it is preferable that, as shown in FIG. 1F, a threading pitch P1 of the first threading part 4 is increased, and the root diameters D1b1 and D1b2 of the male threading are reduced, that is to say, an effective diameter D1e is reduced. This enables implanting the first threading part 4 with favorable implantation torque, and enables realizing physical fixing of the dental implant 51 at the beginning of implantation.

Accordingly, in consideration of the above, the higher the heights H1 and H2 of the thread crests of the first threading part 4 (see FIG. 1F), the more desirable it is. Specifically, it is preferable that the heights H1 and H2 of the thread crests are greater than or equal to 0.25 mm.

It should be noted that the when the heights H1 and H2 of the thread crests are raised, the root diameters D1b1 and D1b2 of the male threading decrease, thus reducing the mechanical strength of the first threading part 4. Also, in consideration of the fact that the inner diameter of the bone hole formed in the jawbone with an implant drill before the dental implant is implanted is ordinarily approximately the effective diameter of the male threading formed at the dental implant sites, if the root diameters D1b1 and D1b2 of the male threading are too low, there is an increase in the space between the dental implant 51 and the jawbone after the dental implant 51 has been implanted, which increases the number of sites that require a longer time to obtain favorable osseointegration. Accordingly, it is preferable that the heights H1 and H2 of the thread crests of the first threading part 4 are less than or equal to 1.2 mm, or more preferably less than or equal to 0.8 mm.

Due to additionally having the above-described shape, the dental implant 51 of Embodiment 1 can be applied to many cases and types of procedures.

It should be noted that the following are countermeasures taken in anomalistic cases. In cases where, for example, all of the sites in the jawbone 30 where the dental implants 51 are to be implanted are soft, or physical fixing force cannot be obtained at the start of implantation in the procedure immediately after tooth removal, it is preferable that, for example, the two-part procedure is selected, and the healing period is extended. Also, in the case of a hard jawbone, it is preferable that the implantation torque used when implanting the dental implant 51 is reduced to an appropriate value by making the bone hole formed by the implant drill slightly larger than normal and/or using the implant drill (tap drill) to form, in the bone hole, thread grooves that have the same pitch as the lead L of the dental implant 51.

It is preferable that the upper limit of the appropriate value of the implantation torque for the dental implant 51 is less than or equal to 50 N·cm, or more preferably less than or equal to 40 N·cm, but there is no particular limitation to this. Also, it is preferable that the lower limit of this appropriate value is greater than or equal to 20 N·cm.

When the dental implant 51 is implanted into the bone hole formed using the implant drill, the second threading part 5 is screwed into the cortical bone 31, and then the implantation torque increasing part 3 is screwed into the cortical bone 31. The lead of the projecting rows 13 constituting the implantation torque increasing part 3 can be thought to be zero. Accordingly, when the projecting rows 13 start to come into contact with and be screwed into the cortical bone 31, the torque necessary for screwing in the dental implant 51 non-continuously (sharply) rises. The practitioner can recognize this non-continuous rise in the torque in a sensory manner. This enables the dental implant 51 to be accurately implanted at the implantation location determined at the time of diagnosis.

Also, as described above, one of the causes of bone resorption (regression) is that bacteria intrudes from the bone surface 35 into the border between the bone and the dental implant and causes erosion toward the tip part along the border between the bone and the dental implant. In this case, the bacteria does not cause erosion along the longitudinal direction of the implant, but rather advances along the grooves formed in the surface of the dental implant. With the dental implant 51 of the present invention, the implantation torque increasing part 3 (i.e., the projecting rows 13) is formed so as to be farthest on the dental crown side. The grooves constituting the projecting rows 13 are not spiral grooves. This enables the delaying of bone resorption (regression), and further has the possibility of preventing bone resorption (regression). Accordingly, the dental implant 51 of Embodiment 1 is advantageous in reducing bone resorption (regression) in the vicinity of the bone surface 35.

If a length L3 of the implantation torque increasing part 3 in the central axis 11 direction (see FIG. 1C) is too long, resistance rises when the implantation torque increasing part 3 is implanted in the jawbone 30, and the torque required to implant the dental implant 51 rises, thus raising the possibility of damaging the jawbone 30 and causing bone resorption (regression). Accordingly, it is preferable that the upper limit of the length L3 of the implantation torque increasing part 3 is less than or equal to 1.0 mm, or more preferably less than or equal to 0.5 mm. On the other hand, if the length L3 of the implantation torque increasing part 3 in the central axis 11 direction is too short, the above-described effect of the implantation torque increasing part 3 decreases, and therefore it is preferable that the lower limit of the length L3 is greater than or equal to 0.1 mm, or more preferably greater than or equal to 0.2 mm.

As described above, the first contour line 16a, on which the tops of the thread crests of the second threading part 5 and the tops of the projecting rows of the projecting rows 13 constituting the implantation torque increasing part 3 are aligned sequentially, is tilted with respect to the central axis 11 such that the distance to the central axis 11 increases with movement toward the dental crown side of the dental implant 51. Accordingly, as the second threading part 5 and the implantation torque increasing part 3 of the dental implant 51 are implanted into the bone, the dental implant 51 increases the diameter of the bone hole, and the implantation torque rises. This enables increasing of the initial physical fixing force of the dental implant 51 with respect to the bone after the dental implant 51 is implanted. This is advantageous to reducing bone resorption (regression). Also, since the first contour line 16a is tilted as described above, there is a more pronounced change in the torque when the implantation torque increasing part 3 starts to be screwed into the cortical bone 31.

If the angle θ1 that the first contour line 16a forms with the central axis 11 is too low, the above-described effects obtained by the tilting of the first contour line 16a are reduced. Accordingly, it is preferable that the lower limit of the angle θ1 is greater than or equal to 0.5 degrees, or more preferably greater than or equal to 1 degree. On the other hand, if the angle θ1 is too high, the resistance and the implantation torque increase when the dental implant 51 is implanted, and there is an increased possibility that the jawbone 30 will be damaged and bone resorption (regression) will occur. Accordingly, it is preferable that the upper limit of the angle θ1 is less than or equal to 8 degrees, or more preferably less than or equal to 4 degrees.

The first threading part 4 and the second threading part 5 that constitute the male threading part 2 have the same lead L. If this lead L is too low, a longer time is required to implant the dental implant 51 at the implantation location determined at the time of diagnosis, and the implantation operation becomes troublesome. Also, the implantation torque ordinarily decreases as the lead L decreases, and conversely increases as the lead L increases. Accordingly, in order to improve efficiency in the operation for implanting the dental implant 51 and to raise the initial physical fixing force of the dental implant 51 with respect to the jawbone 30 after the dental implant 51 is implanted, it is preferable that the lower limit of the lead L is greater than or equal to 0.5 mm, or more preferably greater than or equal to 0.8 mm. On the other hand, in order to prevent damage to the jawbone 30 and the occurrence of bone resorption (regression) due to an increase in the implantation torque, it is preferable that the upper limit of the lead L is less than or equal to 2.4 mm, or more preferably less than or equal to 1.5 mm.

On the other hand, in order to obtain favorable implantation torque, it is preferable that the lower limit of the pitches of the first threading part 4 and the second threading part 5 that constitute the male threading part 2 are greater than or equal to 0.05 mm, or more preferably greater than or equal to 0.1 mm, but there is no particular limitation to this. Also, it is preferable that the upper limit of these pitches is less than or equal to 1 mm, or more preferably less than or equal to 0.25 mm.

It is preferable that the pitch of the first threading part 4 and the pitch of the second threading part 5 are expressed by an integer ratio, and it is more preferable that the pitch of the first threading part 4 is an integral multiple of the pitch of the second threading part 5. This is advantageous to osseointegration between the cortical bone 31 and the second threading part 5.

Figure 2A:
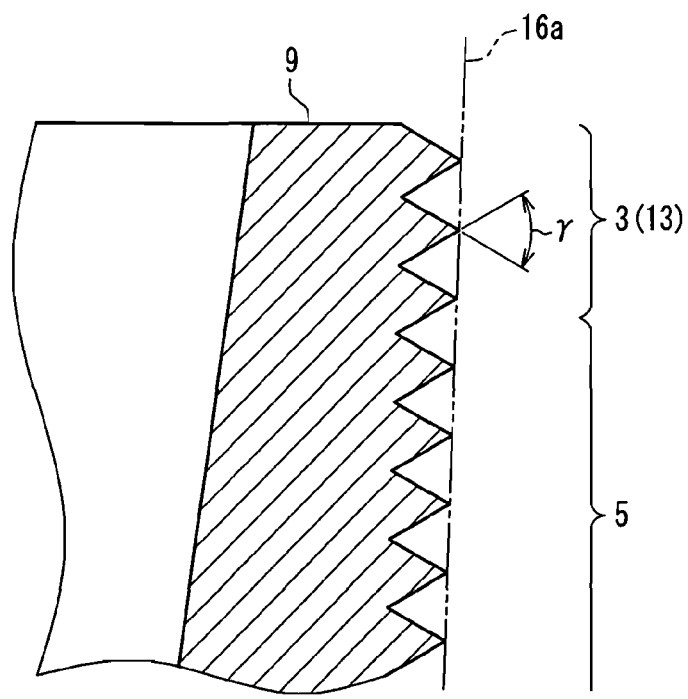
FIG. 2A is an enlarged cross-sectional view of portion A in FIG. 1C that includes an implantation torque increasing part.
Figure 2B:
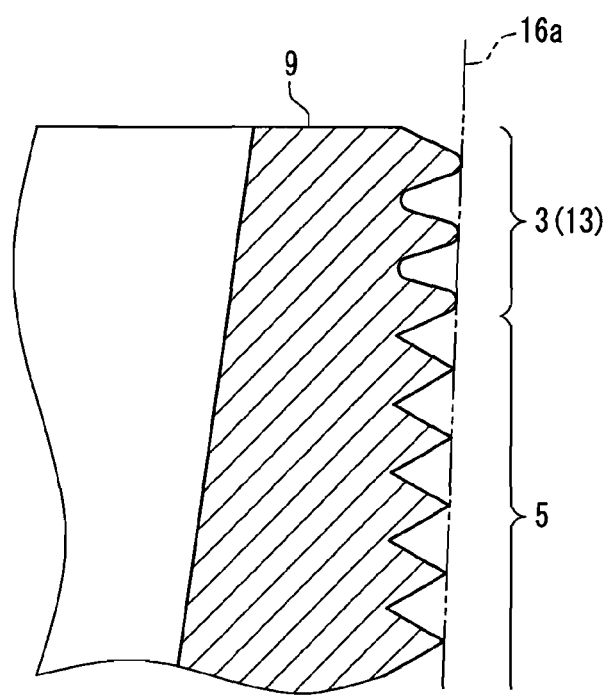
FIG. 2B is an enlarged cross-sectional view showing another cross-sectional shape of multiple projecting rows constituting the implantation torque increasing part.
Figure 2C:
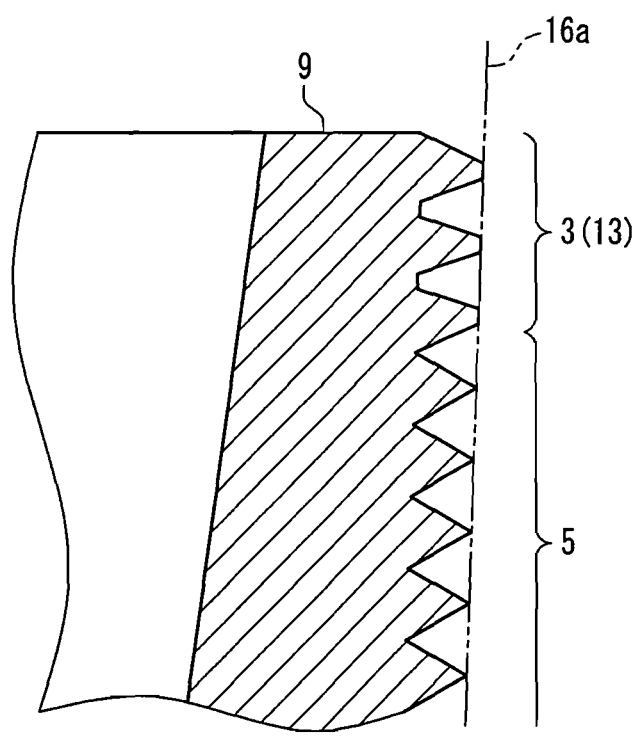
FIG. 2C is an enlarged cross-sectional view showing yet another cross-sectional shape of multiple projecting rows constituting the implantation torque increasing part.

FIG. 2A is an enlarged cross-sectional view of portion A in FIG. 1C that includes the implantation torque increasing part 3. The cross-sectional shape of each projecting row among the projecting rows 13 constituting the implantation torque increasing part 3 is a triangle as shown in FIG. 2A. It should be noted that in the present invention, the cross-sectional shape of the projecting rows among the projecting rows 13 is not limited to this. For example, as shown in FIG. 2B, the triangles may be irregular such that the tops of the projecting rows and the bottoms of the grooves (receding rows) are formed so as to be rounded. Alternatively, as shown in FIG. 2C, a substantially trapezoidal shape is possible in which the tops of the projecting row and the bottoms of the grooves (receding rows) are formed so as to be cylindrical faces or tapered faces. In FIG. 2C, it is preferable that the tops of the projecting rows conform to the first contour line 16a. Of course the cross-sectional shape of the projecting rows 13 may be any other shape. Similarly to the above-described implantation torque increasing part 3, any shape can be adopted for the cross-sectional shape of the teeth of the male threading constituting the male threading part 2.

It should be noted that ordinarily, if the tops of the crests of the male threading are sharp, there is an increased possibility that bone resorption will occur due to the concentration of stress at the portion of the jawbone that corresponds to the tops. Accordingly, it is preferable that processing is carried out such that, for example, the tops of the crests of the male threading are rounded (R-chamfered) as shown in FIG. 2B, cut off (C-chamfered) as shown in FIG. 2C, or subjected to a combination of these.

It is preferable that in a cross-section taken along a plane including the central axis 11, the lower limit of a tip angle $\gamma$ of the teeth of the male threading constituting the male threading part 2 and the projecting rows of the projecting rows 13 constituting the implantation torque increasing part 3 (see FIGS. 1F, 1G, and 2A) is greater than or equal to 20 degrees, or more preferably greater than or equal to 40 degrees, but there is no particular limitation to this. Also, it is preferable that the upper limit of the tip angle $\gamma$ is less than or equal to 90 degrees, or more preferably less than or equal to 70 degrees. If the tip angle $\gamma$ is lower than the above-described lower limit, there is an increased possibility that bone resorption will occur due to the concentration of stress at portions of the jawbone that correspond to the tops of the thread crests or the projecting rows. On the other hand, if the tip angle $\gamma$ is higher than the above-described upper limit, there is a decrease in the surface area where osseointegration with the bone is obtained. Also, in the male threading part 2, it becomes difficult to obtain sufficient thrust when implanting the dental implant 51. Although the tip angle is the same for the first threading part 4, the second threading part 5, and the projecting rows 13 in the above example, at least one of these tip angles may be different from the other tip angles.

The tilt angle $\theta 3$ that the third contour line 18a forms with the central axis 11 in the third region 18 on the tip side is set so as to be relatively higher than the tilt angle $\theta 1$ of the first contour line 16a in the first region 16 such that the tip portion of the dental implant 51 has a tapered shape. Accordingly, the implantation torque decreases so as to enable preventing damage to the jawbone 30 and the occurrence of bone resorption (regression).

Also, a tap groove 15 is formed so as to extend from the tip of the dental implant 51 toward the dental crown side. In the process of implanting the dental implant 51 into the jawbone 30, the tap groove 15 forms female threading on the inner circumferential face of the bone hole formed by the implant drill (self-tapping). Although the tap groove 15 extends obliquely with respect to the central axis 11 in the present example when the dental implant 51 is viewed along a direction orthogonal to the central axis 11 as shown in FIG. 1A, the extending direction of the tap groove 15 is arbitrary and may be parallel with the central axis 11, for example. Also, although two tap grooves 15 are formed at positions symmetric about the central axis 11 in the present example as shown in FIG. 1E, the number of tap grooves 15 may be higher or lower than this. In the case where multiple tap grooves 15 are formed, it is preferable that the tap grooves 15 are arranged at equiangular intervals with respect to the central axis 11.

The material of the dental implant 51 is not limited in any particular way, and a known material can be appropriately selected and used as the dental implant material. Examples includes a metal material such as pure titanium or a titanium allow, and a ceramic material such as alumina or zirconia.

The manufacturing method for the dental implant 51 is also not limited in any particular way, and it is possible to appropriately select a known manufacturing method to be used for dental implant manufacturing. The outer face of the dental implant 51 can be formed by a cutting operation, for example. Regarding the surface texture formed by merely performing a cutting operation (CAM) using a general precision work program (CAD), normally a surface roughness Ra is approximately 0.2 µm or a surface roughness Rz is approximately 2.0 µm, and this surface roughness value is dependent on only the machining marks. This surface texture is not well-suited for osseointegration with bone. Even if the surface roughness Ra or Rz is a high value, a surface merely having a high level difference between surface recessions and projections is not well-suited for macrophage cells (the growth thereon, and osseointegration is not favorable.

Accordingly, in order to obtain favorable osseointegration, the surface of the implantation portion 1 needs to be a suitably rough surface. Specifically, it is preferable that the surface roughness Ra is greater than or equal to 0.5 µm and the surface roughness Rz is greater than or equal to 5.0 µm, and it is furthermore preferable that the surface roughness Ra is in the range of 1.15 to 4.05 µm inclusive and the surface roughness Rz is in the range of 5.0 to 40 µm inclusive, which is the standard for screw-type implants according to the standards for approval of dental implants established by the Ministry of Health, Labour, and Welfare of Japan (Food and drug development Clause 0525004).

The surface processing method for obtaining such a surface is not limited in any particular way, and it is possible to appropriately select and use a known surface processing method. Examples of such methods include electrical discharge machining, sandblasting, acid treatment, alkali treatment, anodizing, and coating treatment using calcium phosphate or the like.

Figure 3:
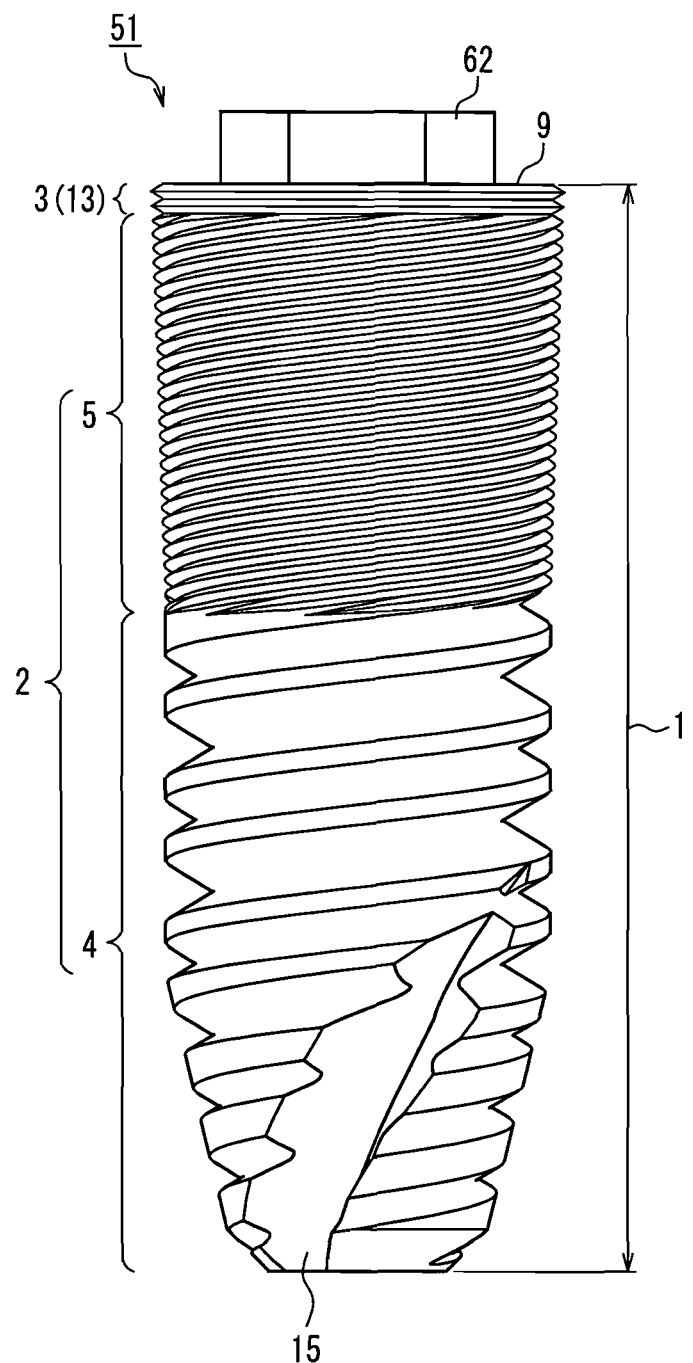
FIG. 3 is a side view of an example of an external fitting dental implant according to Embodiment 1 of the present invention.

As shown in FIG. 1C, a cavity 60 that opens toward the dental crown side is formed in the dental implant 51. The abutment (not shown) is inserted into the cavity 60 and fitted with the cavity 60. In other words, the dental implant 51 of Embodiment 1 is a so-called internal fitting type of dental implant in which the fitting site for the fixture and the abutment is located inside the cavity 60 formed so as to be a recession in the fixture. It should be noted that the dental implant of the present invention is not limited to such an internal fitting type of dental implant, and may be an external fitting type of dental implant in which the fitting site for the fixture and the abutment is provided outward of the fixture (normally upward of the dental crown-side end 9). FIG. 3 is a side view of an example of an external fitting dental implant 51, and in this example, a projection part 62 that protrudes upward beyond the dental crown-side end 9 is fit with the abutment (not shown). Similarly to the internal fitting type of dental implant, the external fitting type of dental implant can also be applied to both a two-piece or three-piece type of dental implant.

Figure 4:
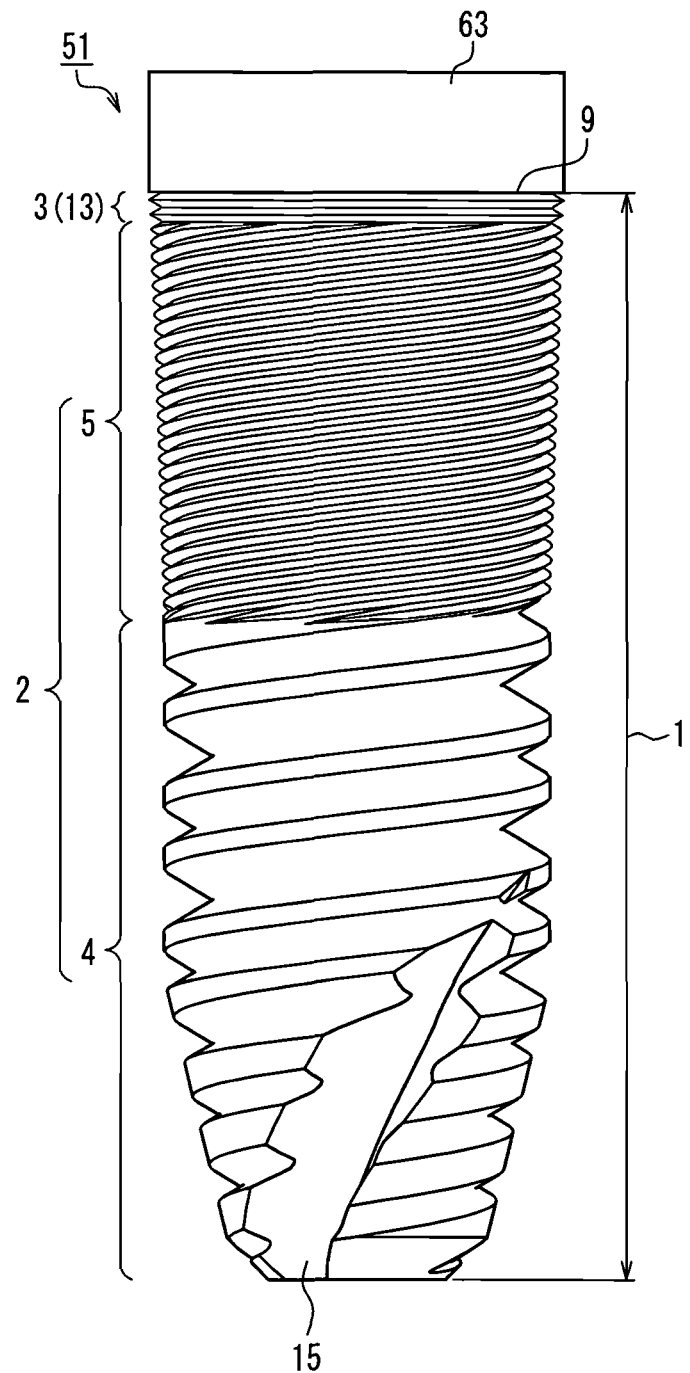
FIG. 4 is a side view of an example of the dental implant according to Embodiment 1 of the present invention that has been provided with a portion that comes into contact with gum tissue.

As shown in FIG. 4, the dental implant 51 may include a portion (hereinafter referred to as the "cuff part") 63 that both penetrates and comes into contact with the gum tissue upward of the implantation portion 1 that is implanted in the jawbone. Regarding the surface texture of the outer face of the cuff part 63, there is no need for the outer face to be a rough face as with the above-described outer face of the implantation portion 1, and it is possible to appropriately select and use a known surface texture such as a smooth surface or a mirror surface. Also, there are no particular limitations on the shape of the cuff part 63. Although FIG. 4 shows the example where the internal fitting dental implant of Embodiment 1 is provided with the cuff part 63, the external fitting dental implant of Embodiment 1 similarly may be provided with the cuff part 63 (not shown).

Figure 5:
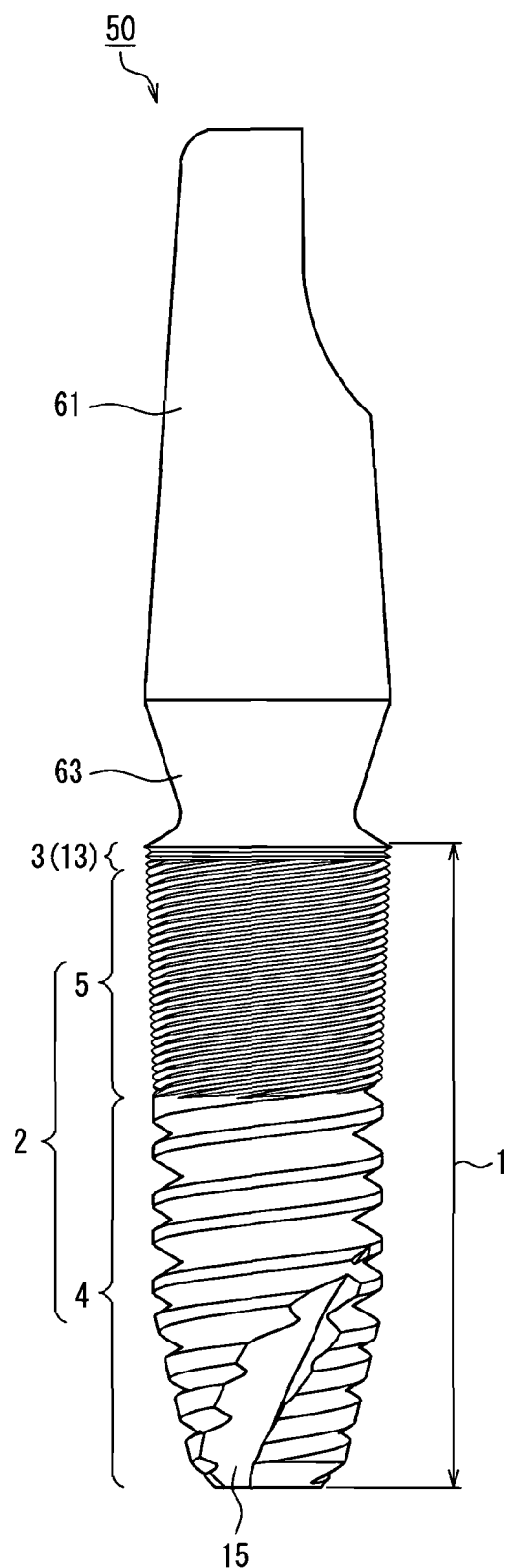
FIG. 5 is a side view of an example of a one-piece dental implant according to Embodiment 1 of the present invention.

The above-described dental implant 51 can be used as the fixture of a two-piece type of dental implant that is constituted by two parts, namely a fixture serving as the dental root replacement and an abutment serving as the dental crown anchor replacement, or a three-piece type of dental implant that is constituted by three parts, namely a fixture, an abutment, and a screw for fixing the abutment to the fixture. It should be noted that the dental implant of the present invention is not limited to a two-piece type or three-piece type of dental implant, and for example, as shown in FIG. 5, the present invention can also be applied to a one-piece type of dental implant in which an abutment 61 is integrated with the fixture serving as the dental root replacement. In FIG. 5, the cuff part 63 that both penetrates and comes into contact with the gum tissue, which was described with reference to FIG. 4, is provided between the abutment 61 and the implantation portion 1 that is implanted in the jawbone.

There are no particular limitations on the applications of the dental implant 51 of Embodiment 1. Possible applications include a dental implant used as a replacement for a lost tooth, a so-called temporary implant used as, for example, a fixing base for an orthodontic wire, and a dental implant used for any other application.

Also, there are no particular limitations on the type of procedure used with the dental implant 51, and examples of applications to known procedures include the following: a two-part procedure in which the dental implant 51 is implanted and the gum tissue is sutured such that the dental implant 51 is not exposed inside the oral cavity, and then a healing period is provided before a prosthesis is attached; and a one-part procedure in which the gum tissue surrounding the dental implant 51 is sutured so as to leave the implanted dental implant 51 exposed.

In actual dental practice, the dental implant specifications and type of procedure are selected depending on various jawbone conditions and the environment inside the oral cavity. In general, the dental implant specifications and types of procedures have advantages and disadvantages, such as the fact that the range of dental implant clinical application becomes narrower when the operability of a dental implant is improved, and the fact that the operability of a dental implant becomes troublesome when using a dental implant having a wide range of clinical application. The dental implant 51 of Embodiment 1 can be used in a broad range, regardless of the specifications and procedure type.

Embodiment 2

Embodiment 2 differs from Embodiment 1 with respect to the configuration of the implantation torque increasing part 3. The following is a description of Embodiment 2 focusing on differences from Embodiment 1. In the drawings referenced in the following description, elements the same as those in Embodiment 1 are denoted by the same reference numerals as those in Embodiment 1, and descriptions thereof will not be given.

Figure 6A:
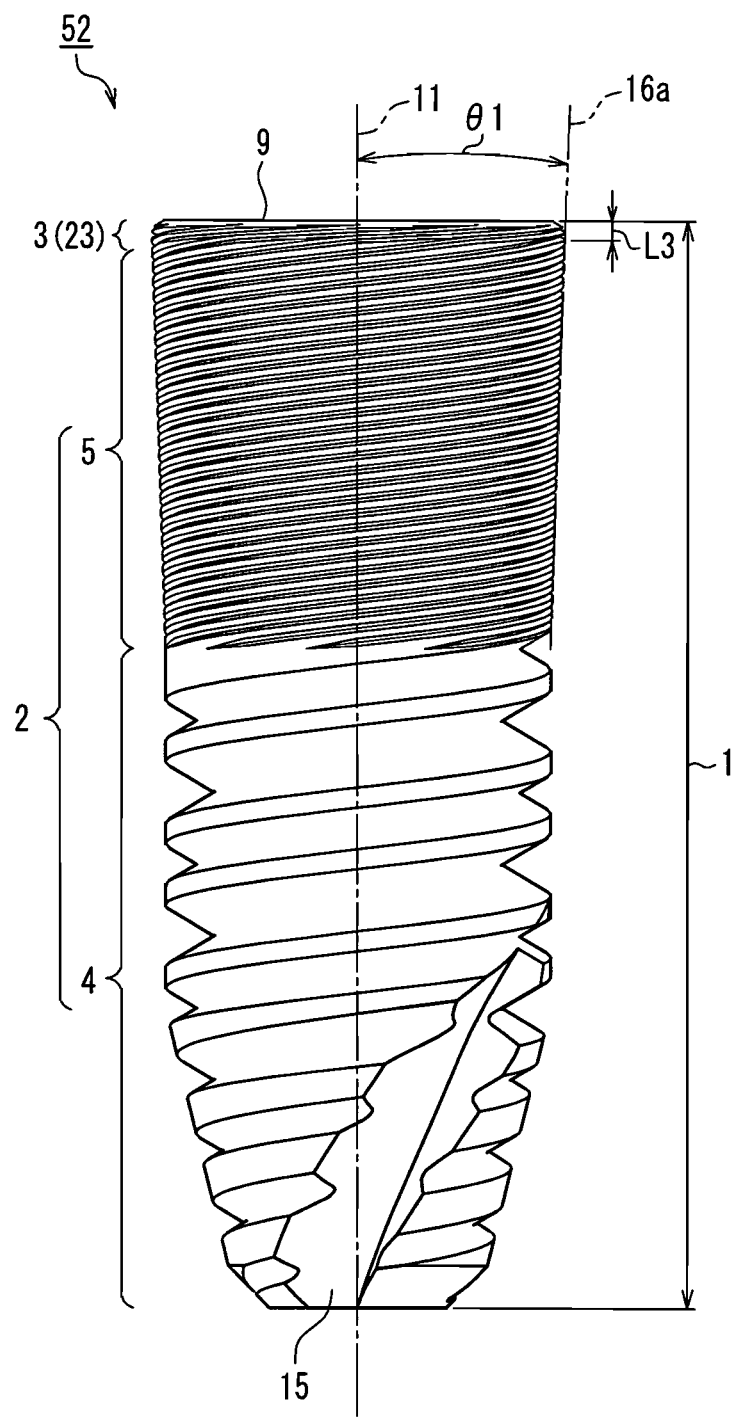
FIG. 6A is a side view of a dental implant according to Embodiment 2 of the present invention.
Figure 6B:
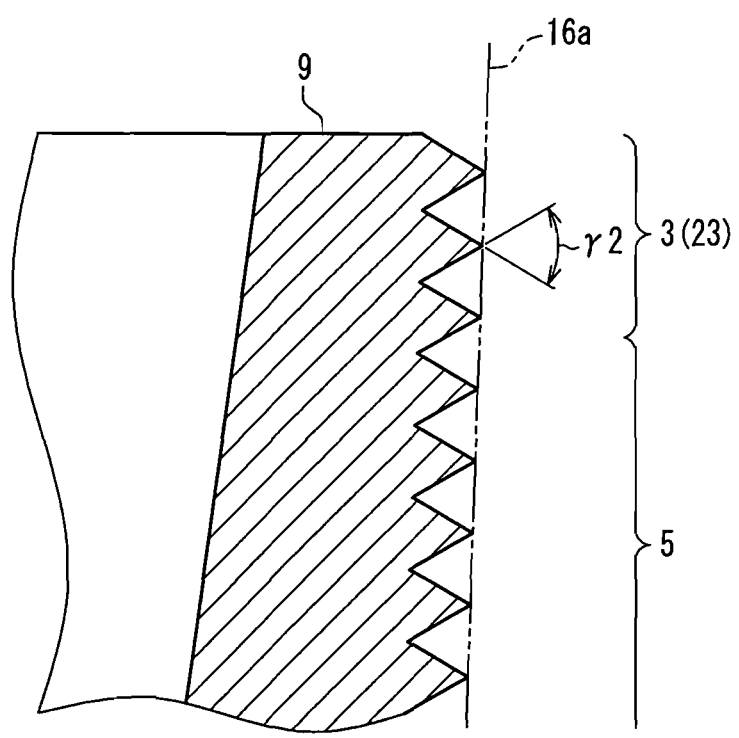
FIG. 6B is an enlarged cross-sectional view of an implantation torque increasing part of the dental implant according to Embodiment 2 of the present invention and its surroundings.

FIG. 6A is a side view of a dental implant 52 according to Embodiment 2. FIG. 6B is an enlarged cross-sectional view of the implantation torque increasing part 3 of the dental implant 52 according to Embodiment 2 and its surroundings, the cross-section having been taken along a plane that includes the central axis 11. In Embodiment 2, the implantation torque increasing part 3 is constituted by minute male threading 23 that is coaxial with the central axis 11 of the dental implant 52. The minute male threading 23 is male threading made up of thread crests whose lead is smaller than the lead of the male threading part 2. It is preferable that the pitch of the minute male threading 23 is lower than the pitch of the second threading part 5 that is adjacent to the minute male threading 23. The winding direction of the minute male threading 23 is the same as the winding direction of the threading part that constitutes the male threading part 2.

Similarly to Embodiment 1, with Embodiment 2 as well, the first contour line 16a that connects the tops of the thread crests of the second threading part 5 in order in the central axis 11 direction is a straight line. Also, the tops of the thread crests of the minute male threading 23 are located on an extension line of the first contour line 16a.

The lead of the minute male threading 23 constituting the implantation torque increasing part 3 is lower than the lead of the second threading part 5. Accordingly, when the minute male threading 23 starts to come into contact with and be screwed into the cortical bone 31 when the dental implant 52 is implanted into the bone hole formed using an implant drill, the torque required to screw in the dental implant 52 increases non-continuously (i.e., sharply). The practitioner can recognize this non-continuous rise in the torque in a sensory manner. This enables the dental implant 52 to be accurately implanted at the implantation location determined at the time of diagnosis, similarly to Embodiment 1.

Also, bacteria that intrudes from the bone surface into the border between the bone and the dental implant 52 advances along the thread grooves of the minute male threading 23. Since the lead of the minute male threading 23 is lower than the lead of the male threading part 2, the minute male threading 23 of Embodiment 2 can also delay bone resorption (regression), similarly to the projecting rows 13 of the Embodiment 1. Accordingly, the dental implant 52 of Embodiment 2 is advantageous in reducing bone resorption (regression) in the vicinity of the bone surface.

The description of the cross-sectional shape of the projecting rows and grooves (receding rows) of the projecting rows 13 of Embodiment 1 (see FIGS. 2A to 2C) similarly applies to the cross-sectional shape of the thread teeth of the minute male threading 23. Also, the description of the tip angle γ of the projecting rows of the projecting rows 13 of Embodiment 1 similarly applies to a tip angle γ2 of the thread crests (see FIG. 6B).

Aspects of Embodiment 2 other than those described above are the same as in Embodiment 1. The description of Embodiment 1 applies to Embodiment 2 as well, either directly or with appropriate modifications.

Embodiment 3

Embodiment 3 differs from Embodiment 1 with respect to the configuration of the implantation torque increasing part 3. The following is a description of present Embodiment 3 focusing on differences from Embodiment 1. In the drawings referenced in the following description, elements the same as those in Embodiment 1 are denoted by the same reference numerals as those in Embodiment 1, and descriptions thereof will not be given.

Figure 7A:
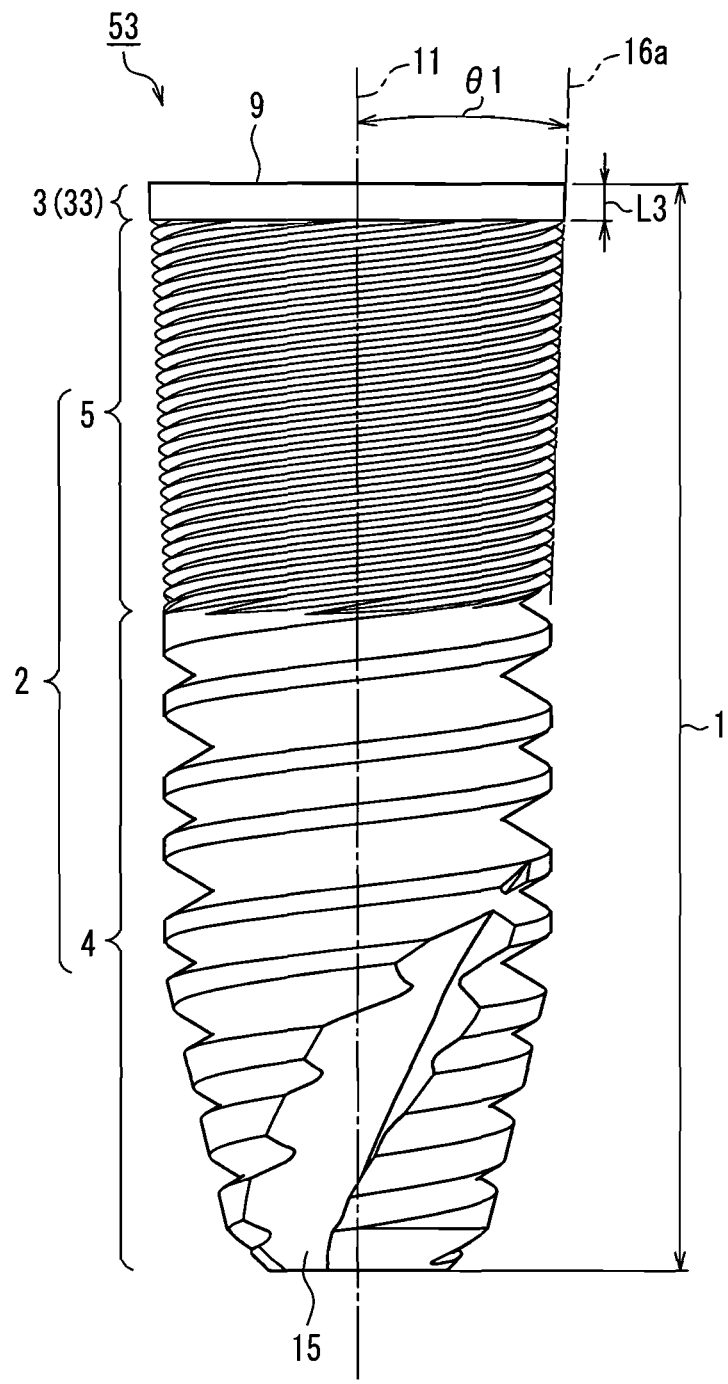
FIG. 7A is a side view of a dental implant according to Embodiment 3 of the present invention.
Figure 7B:
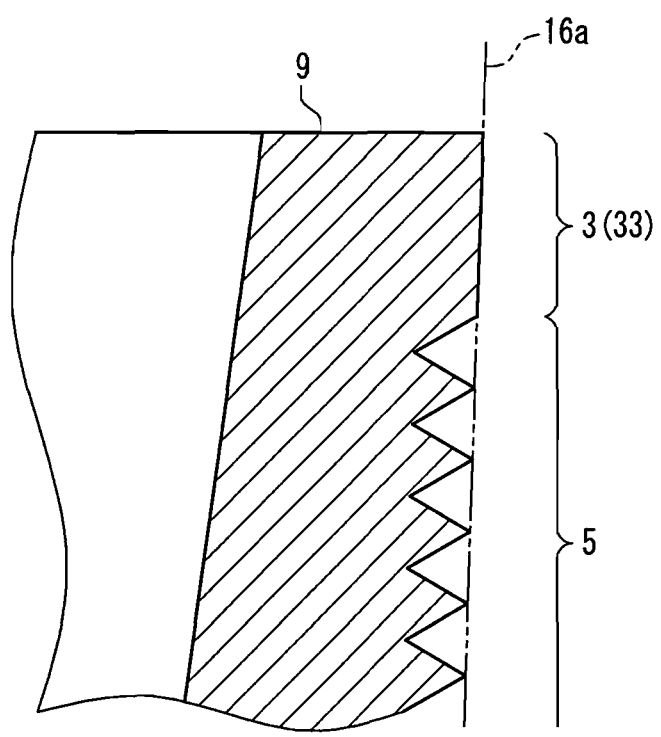
FIG. 7B is an enlarged cross-sectional view of an implantation torque increasing part of the dental implant according to Embodiment 3 of the present invention and its surroundings.

FIG. 7A is a side view of a dental implant 53 according to Embodiment 3. FIG. 7B is an enlarged cross-sectional view of the implantation torque increasing part 3 of the dental implant 53 according to Embodiment 3 and its surroundings, the cross-section having been taken along a plane that includes the central axis 11. In Embodiment 3, the implantation torque increasing part 3 is constituted by one projecting row 33 that is continuous in the circumferential direction of the dental implant 53. The outer circumferential face of the projecting row 33 is a conical face (tapered face) that is coaxial with the central axis 11 of the dental implant 53.

Similarly to Embodiment 1, with Embodiment 3 as well, the first contour line 16a that connects the tops of the thread crests of the second threading part 5 in order in the central axis 11 direction is a straight line. Also, the top of the projecting row 33 (i.e., the conical face) is located on an extension line of the first contour line 16a. In other words, the generatrix of the conical face surrounding the projecting row 33 conforms to the first contour line 16a.

When the projecting row 33 starts to come into contact with and be screwed into the cortical bone when the dental implant 53 is implanted into the bone hole formed using an implant drill, the torque required to screw in the dental implant 53 increases non-continuously (i.e., sharply). The practitioner can recognize this non-continuous rise in the torque in a sensory manner. This enables the dental implant 53 to be accurately implanted at the implantation location determined at the time of diagnosis, similarly to Embodiment 1.

Note that in Embodiment 3, grooves such as those in Embodiments 1 and 2 are substantially not formed in the implantation torque increasing part 3. Accordingly, the effect of preventing bone resorption (regression) caused by bacteria that has intruded from the bone surface into the border between the bone and the dental implant 53 is lower in Embodiment 3 than in Embodiments 1 and 2.

Aspects of Embodiment 3 other than those described above are the same as in Embodiment 1. The description of Embodiment 1 applies to Embodiment 3 as well, either directly or with appropriate modifications.

Embodiment 4

Embodiment 4 differs from Embodiment 1 with respect to the configuration of the implantation torque increasing part 3. The following is a description of present Embodiment 4 focusing on differences from Embodiment 1. In the drawings referenced in the following description, elements the same as those in Embodiment 1 are denoted by the same reference numerals as those in Embodiment 1, and descriptions thereof will not be given.

Figure 8A:
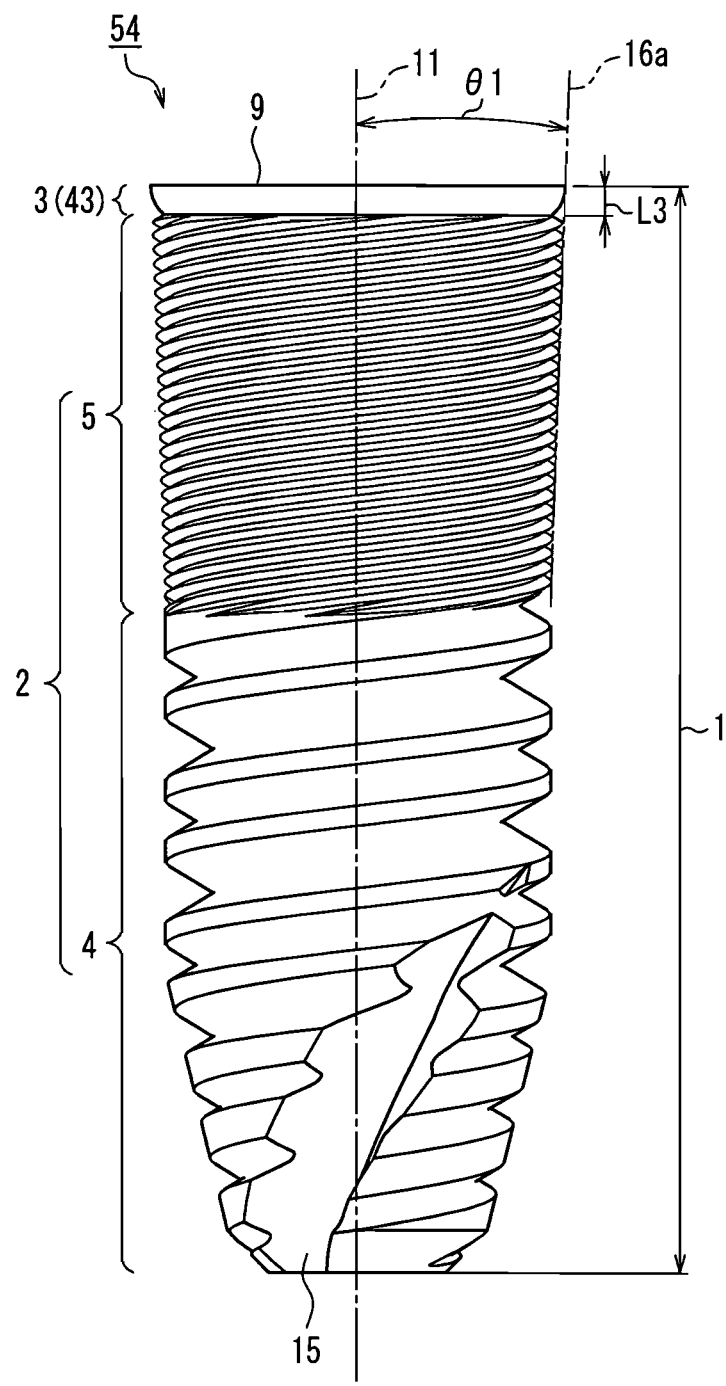
FIG. 8A is a side view of a dental implant according to Embodiment 4 of the present invention.
Figure 8B:
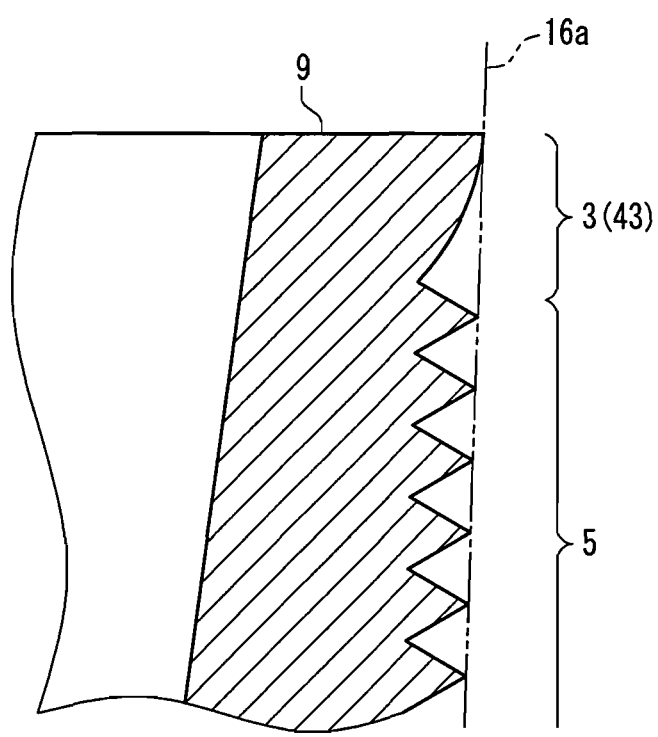
FIG. 8B is an enlarged cross-sectional view of an implantation torque increasing part of the dental implant according to Embodiment 4 of the present invention and its surroundings.

FIG. 8A is a side view of a dental implant 54 according to Embodiment 4. FIG. 8B is an enlarged cross-sectional view of the implantation torque increasing part 3 of the dental implant 54 according to Embodiment 4 and its surroundings, the cross-section having been taken along a plane that includes the central axis 11. In Embodiment 4, the implantation torque increasing part 3 is constituted by one projecting row 43 that is continuous in the circumferential direction of the dental implant 54. As shown in FIG. 8B, the cross-sectional shape of the outer circumferential face of the projecting row 43 is substantially a circular arc. The outer diameter of the projecting row 43 is the highest at the dental crown-side end 9.

Similarly to Embodiment 1, with Embodiment 4 as well, the first contour line 16a that connects the tops of the thread crests of the second threading part 5 in order in the central axis 11 direction is a straight line. Also, the top of the projecting row 43 (i.e., the portion forming the largest diameter) is located on an extension line of the first contour line 16a.

When the projecting row 43 starts to come into contact with and be screwed into the cortical bone when the dental implant 54 is implanted into the bone hole formed using an implant drill, the torque required to screw in the dental implant 54 increases non-continuously (i.e., sharply). The practitioner can recognize this non-continuous rise in the torque in a sensory manner. This enables the dental implant 54 to be accurately implanted at the implantation location determined at the time of diagnosis, similarly to Embodiment 1.

Note that in Embodiment 4, grooves such as those in Embodiments 1 and 2 are substantially not formed in the implantation torque increasing part 3. Accordingly, the effect of preventing bone resorption (regression) caused by bacteria that has intruded from the bone surface into the border between the bone and the dental implant 54 is lower in Embodiment 4 than in Embodiments 1 and 2.

Aspects of Embodiment 4 other than those described above are the same as in Embodiment 1. The description of Embodiment 1 applies to Embodiment 4 as well, either directly or with appropriate modifications.

Embodiment 5

Figure 9:
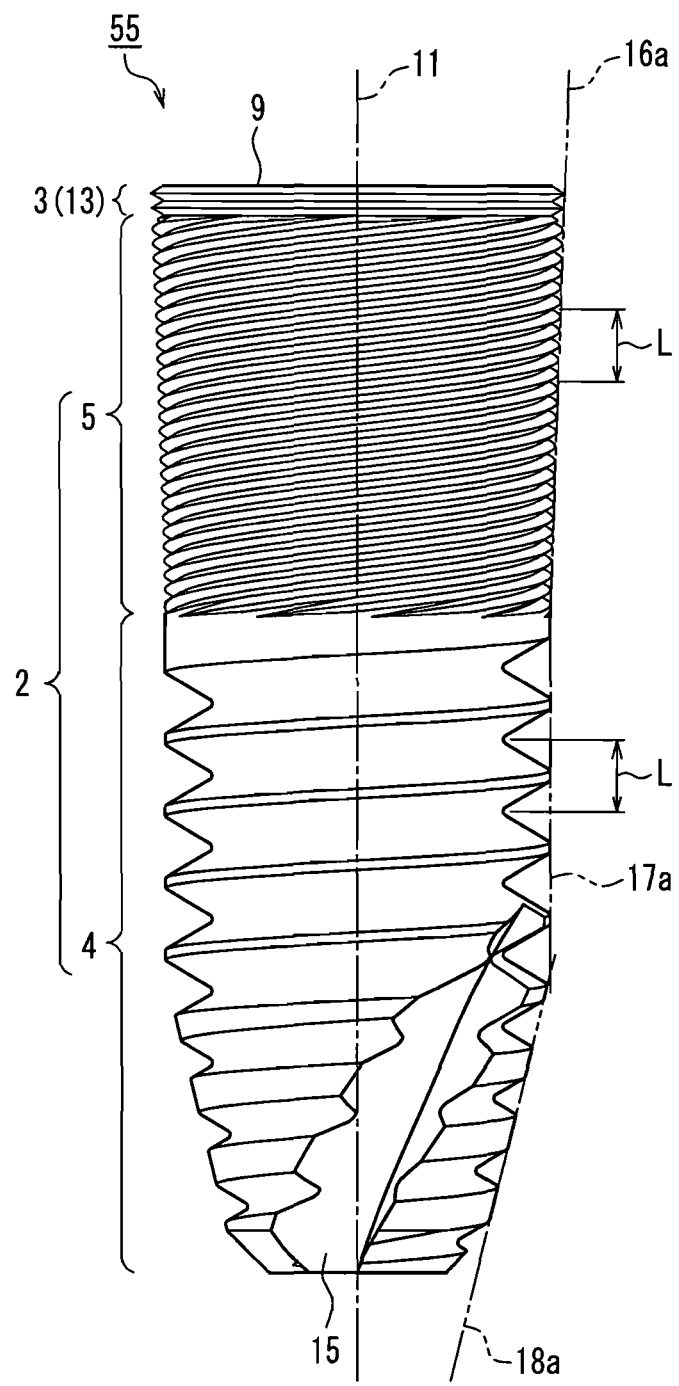
FIG. 9 is a side view of a dental implant according to Embodiment 5 of the present invention.

FIG. 9 is a side view of a dental implant 55 according to Embodiment 5 of the present invention. Whereas double-start thread made up of two spiral grooves having different root diameters is formed in the first threading part 4 in Embodiment 1, single-start thread made up of one spiral groove is formed in the first threading part 4 in Embodiment 5. Multiple-start thread is formed in the second threading part 5 so as have the same lead as the lead L of the first threading part 4 and a pitch lower than the pitch of the first threading part 4. In Embodiment 5, the lead of the male threading part 2 is generally lower than that in Embodiment 1.

Although FIG. 9 shows an example in which the first threading part 4 is changed to single-start thread, the present invention is not limited to this, and multiple-start thread such as triple-start thread or higher may be formed in the first threading part 4. Regardless of the number of rows in the first threading part 4, the male threading that is formed in the second threading part 5 has the same lead as that of the first threading part 4 and a lower pitch.

Aspects of Embodiment 5 other than those described above are the same as in Embodiment 1.

Although the example of changing the configuration of the first threading part 4 of Embodiment 1 is described above, a similar modification can be applied to Embodiments 2 to 4 as well.

Embodiment 6

Figure 10:
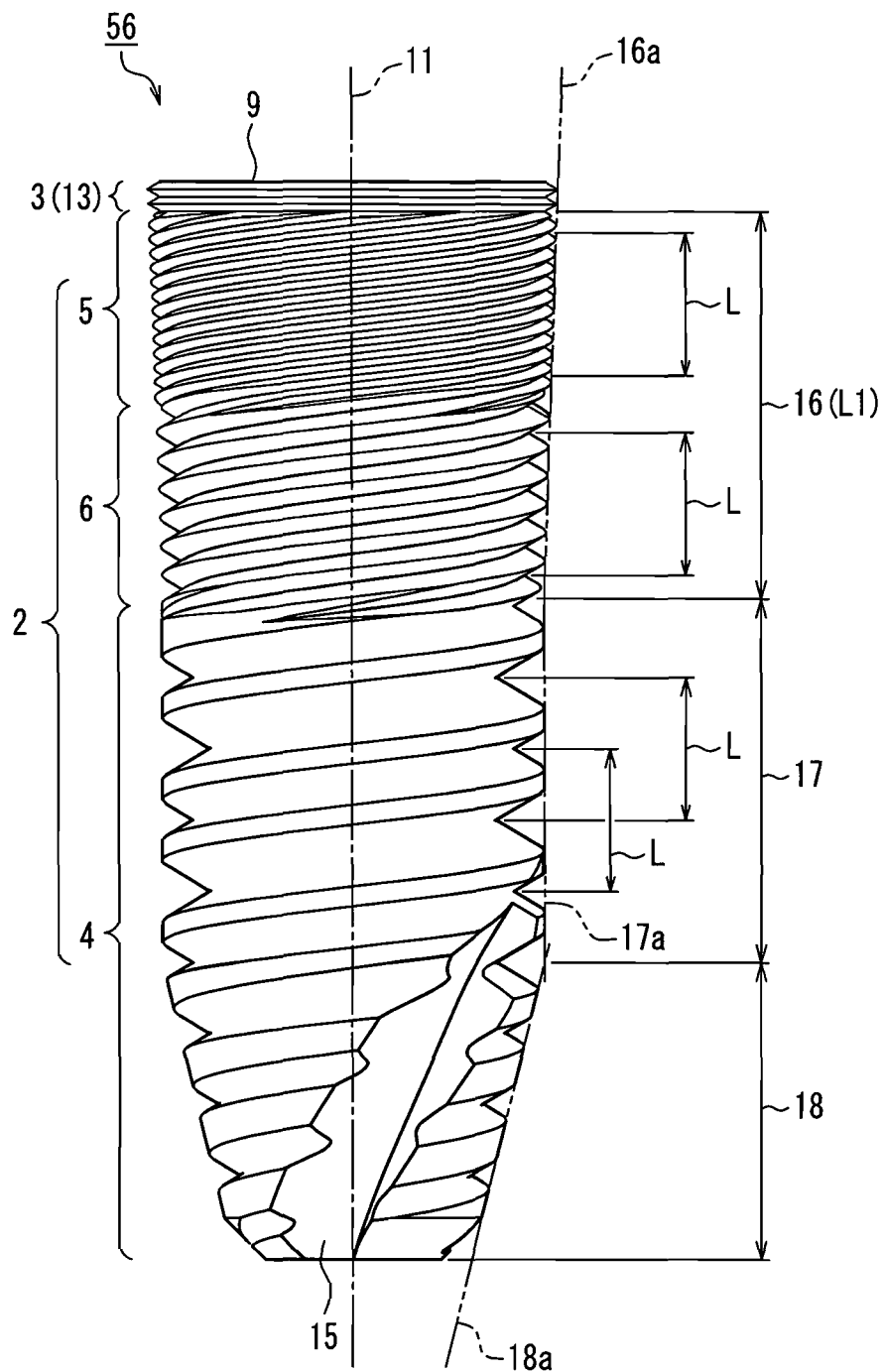
FIG. 10 is a side view of a dental implant according to Embodiment 6 of the present invention.

FIG. 10 is a side view of a dental implant 56 according to Embodiment 6 of the present invention. Whereas the male threading part 2 is constituted by two threading parts (the first threading part 4 and the second threading part 5) in Embodiment 1, the male threading part 2 is constituted by three threading parts (the first threading part 4, the second threading part 5, and a third threading part 6) in Embodiment 6. The male threading that is formed in the first threading part 4 and the second threading part 5 of Embodiment 6 have the same lead, pitch, and number of rows as the male threading formed in the first threading part 4 and the second threading part 5 of Embodiment 1. The third threading part 6 is arranged between the first threading part 4 and the second threading part 5. Multiple-start thread is formed in the third threading part 6 so as to have the same lead as that of the first threading part 4 and the second threading part 5, and a pitch that is lower than that of the first threading part 4 and higher than that of the second threading part 5. As described in Embodiment 1, it is preferable that that the pitches of the first threading part 4, the second threading part 5, and the third threading part 6 are expressed by an integer ratio, and it is more preferable that the pitch of the first threading part 4 is an integral multiple of each of the pitches of the second threading part 5 and the third threading part 6.

Similarly to Embodiment 1, the first contour line 16*a* that connects the tops of the thread crests of the second threading part 5 in order in the central axis 11 direction is a straight line, and the tops of the projecting rows of the projecting rows 13 constituting the implantation torque increasing part 3 are located on an extension line extending upward from the first contour line 16*a*.

Also, the tops of the thread crests of the third threading part 6 are located on an extension line extending downward from the first contour line 16*a*. Accordingly, in Embodiment 6, the first region 16 corresponds to the area formed by the second threading part 5 and the third threading part 6.

In the present example, it is preferable that the implantation torque increasing part 3 and the first region 16 (the second threading part 5 and the third threading part 6) engage with the cortical bone, and the second region 17 and the third region 18 (the first threading part 4) engage with the cancellous bone 32.

Accordingly, as described in Embodiment 1, it is preferable that the length L1 of the first region 16 (i.e., the second threading part 5 and the third threading part 6 in Embodiment 6) in the central axis 11 direction is greater than or equal to 2.0 mm, or more preferably in the range of 3.2 mm to 4.0 mm inclusive.

In Embodiment 6, the third threading part 6 is provided between the first threading part 4 and the second threading part 5, thus enabling a reduction in the change in the implantation torque that occurs due to change in the pitch when the dental implant 56 is implanted.

Although FIG. 10 shows an example in which the male threading part 2 is constituted by three types of threading parts that have the same lead but different pitches, the number of types of threading parts that constitute the male threading part 2 is not limited to this, and four or more types of threading parts may be provided. Regardless of the number of types of threading parts that constitute the male threading part 2, the threading parts are arranged in order of their pitches, such that the pitch increases toward the tip side. The leads of the all of the threading parts that constitute the male threading part 2 are all set the same, and the winding directions of all of the threading parts are all set the same.

Aspects of Embodiment 6 other than those described above are the same as in Embodiment 1.

Although the example where the male threading part 2 of Embodiment 1 is constituted by three or more types of threading parts is described above, Embodiment 6 can be applied to the male threading part 2 of Embodiments 2 to 5 as well.

Embodiment 7

Figure 11:
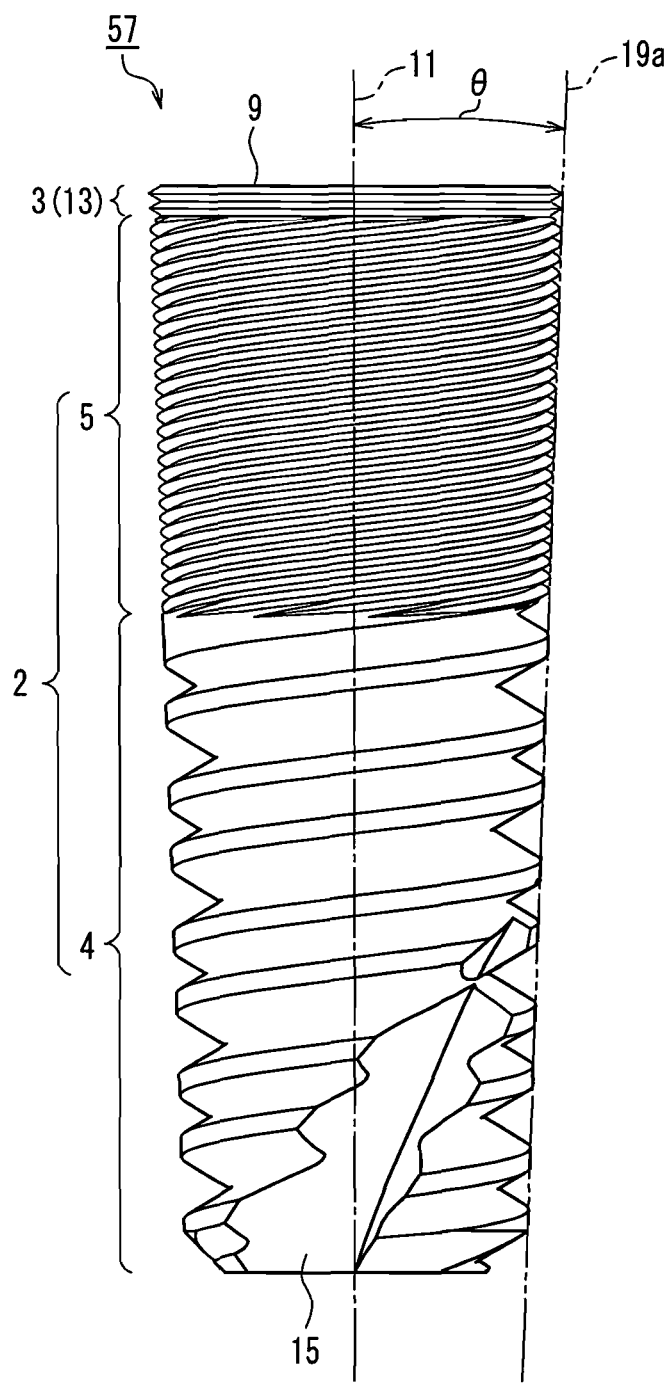
FIG. 11 is a side view of a dental implant according to Embodiment 7 of the present invention.

FIG. 11 is a side view of a dental implant 57 according to Embodiment 7 of the present invention. Whereas the outer form (contour shape) of the dental implant 51 of Embodiment 1 has three contour lines (the first contour line 16*a*, the second contour line 17*a*, and the third contour line 18*a*) that have different tilts with respect to the central axis 11, the outer form (contour shape) of the dental implant 57 of Embodiment 7 has substantially only one contour line 19*a*. Specifically, the implantation torque increasing part 3 and the male threading part 2 are formed on a single tapered face (conical face) whose generatrix is the contour line 19*a*. The contour line 19*a* is tilted at the angle θ with respect to the central axis 11 such that the distance to the central axis 11 decreases with movement toward the tip side of the dental implant 57.

Although FIG. 11 shows an example where the outer form of the dental implant 57 has a single contour line, the outer form of the dental implant may have four or more contour lines. Regardless of the number of contour lines, all of the contour lines are tilted such that the distance to the central axis 11 decreases toward the lower side or are parallel with the central axis 11. The outer form of the dental implant is set so as to follow the contour line(s). Accordingly, the outer diameter of the dental implant increases toward the dental crown side.

Aspects of Embodiment 7 other than those described above are the same as in Embodiment 1.

Although the example of changing the outer form (contour shape) of the dental implant 51 of Embodiment 1 is described above, a similar modification can be applied to Embodiments 2 to 6 as well.

Embodiment 8

Figure 12:
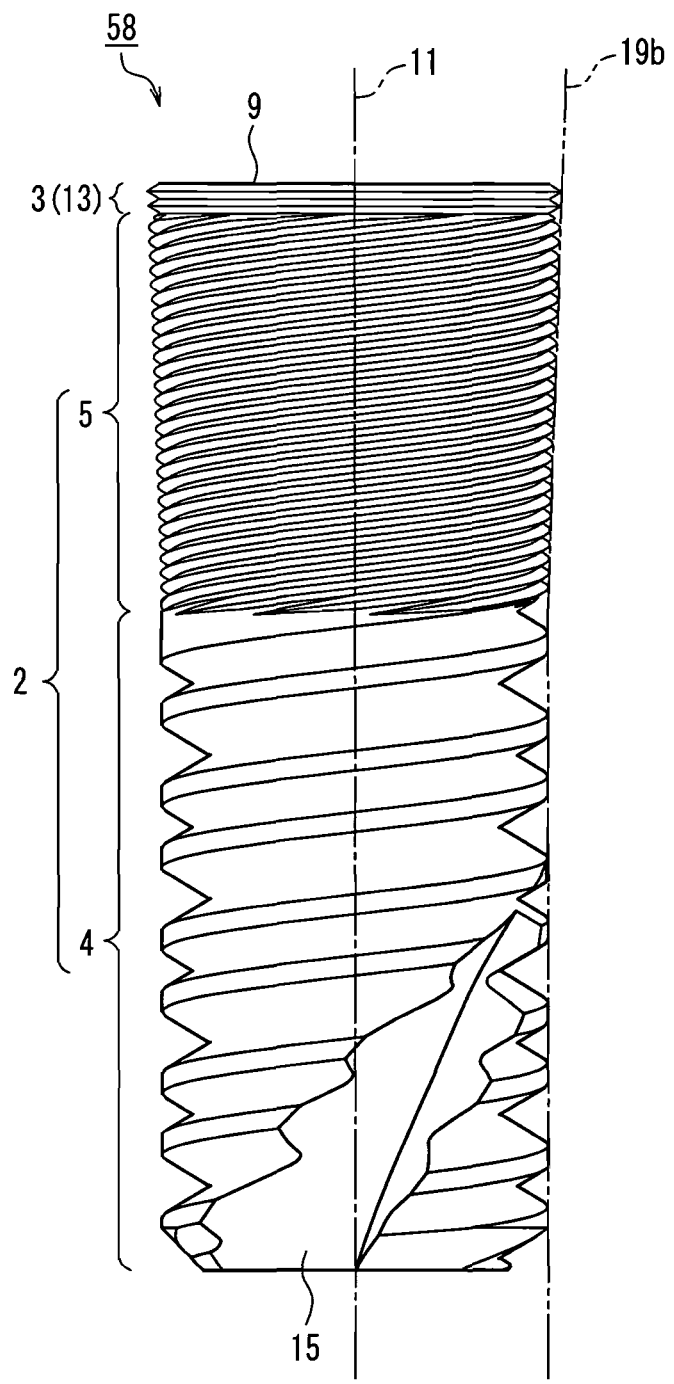
FIG. 12 is a side view of a dental implant according to Embodiment 8 of the present invention.

FIG. 12 is a side view of a dental implant 58 according to Embodiment 8 of the present invention. Whereas the contour line 19*a* is tilted at the angle θ (θ>0 degrees) with respect to the central axis 11 in the dental implant 57 of FIG. 11 that is described in Embodiment 7, a contour line 19*b* is parallel with the central axis 11 in the dental implant 58 of Embodiment 8. Specifically, the implantation torque increasing part 3 and the male threading part 2 are formed on a cylindrical face that is coaxial with the central axis 11. Accordingly, the outer diameter of the dental implant 58 is constant along the central axis 11 direction.

Aspects of Embodiment 8 other than those described above are the same as in Embodiment 1.

Although the example of changing the outer form (contour shape) of the dental implant 51 of Embodiment 1 is described above, a similar modification can be applied to Embodiments 2 to 6 as well.

Embodiment 9

Figure 13:
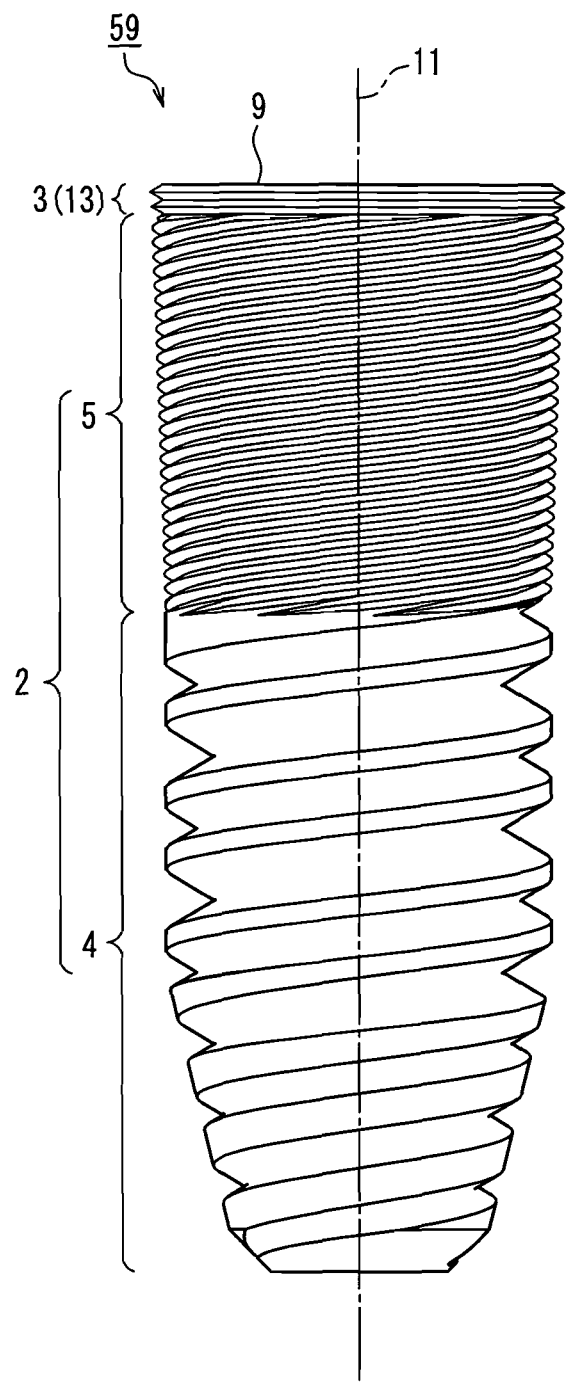
FIG. 13 is a side view of a dental implant according to Embodiment 9 of the present invention.

FIG. 13 is a side view of a dental implant 59 according to Embodiment 9 of the present invention. Whereas the tap grooves 15 are formed in the dental implant 51 of Embodiment 1, tap grooves are not formed in the dental implant 59 of Embodiment 9. The dental implant 59 of Embodiment 9 preferably can be used in the case of implantation into a bone hole in which a thread groove has been formed in advance using an implant drill (tap drill).

Aspects of Embodiment 9 other than those described above are the same as in Embodiment 1.

Although the example of omitting tap grooves from the dental implant 51 of Embodiment 1 is described above, tap grooves may be similarly omitted from the dental implants of Embodiments 2 to 8.

The embodiments described above are all merely intended to clarify the technical content of the present invention, and the present invention is not intended to be interpreted as being limited only these specific examples. Various modifications can be carried out within the scope recited in the claims, and all such modifications are encompassed in the present invention.

A dental implant of the present invention can be applied in a broad range regardless of jawbone conditions and the environment in oral cavity, has wide clinical applicability, and has broad utility. Also, it is possible for the dental implant to be accurately implanted at the implantation location determined at the time of diagnosis. Furthermore, bone resorption (regression) in the vicinity of the bone end can be reduced by appropriately selecting the configuration of the implantation torque increasing part. The present invention therefore can be widely used in the field of dental implants.

DESCRIPTION OF REFERENCE CHARACTERS 1 implantation portion
2 male threading part
3 implantation torque increasing part
4 first threading part
5 second threading part
6 third threading part
9 dental crown-side end (bone end)
11 central axis of dental implant
13 projecting rows (implantation torque increasing part)
15 tap groove
16 first region
16a first contour line
17 second region
17a second contour line
18 third region
18a third contour line
19a, 19b contour line
23 minute male threading (implantation torque increasing part)
30 jawbone
31 cortical bone
32 cancellous bone
33, 43 projecting row (implantation torque increasing part)
35 bone surface
51-59 dental implant
60 cavity
61 abutment
62 projection part
63 cuff part

What is claimed is:

1. A dental implant for implantation in a jawbone, comprising:
a male threading part and an implantation torque increasing part on an outer face of the dental implant in the stated order away from a tip side along the direction of a central axis of the dental implant, the male threading part and the implantation torque increasing part being coaxial with the central axis,
wherein the male threading part includes a plurality of threading parts that have the same lead and different pitches,
the plurality of threading parts are arranged in order of pitch magnitude such that the pitch increases toward the tip side,
the outer diameter of the male threading part is constant in the central axis direction or increases toward the implantation torque increasing part,
the implantation torque increasing part includes a plurality of non-spiral projecting rows that are continuous in the circumferential direction,
the plurality of threading parts includes an adjacent threading part located immediately next to the implantation torque increasing part, the adjacent threading part includes two or more thread revolutions that have identical pitches,
in a cross-section that includes the central axis, the adjacent threading part have two or more thread crests, and the plurality of non-spiral projecting rows have a plurality of tops, all tops of the thread crests of the adjacent threading part and all of the tops of the plurality of non-spiral projecting rows of the implantation torque increasing part are located on a common straight line,
the dental implant is configured so that the plurality of non-spiral projecting rows of the implantation torque increasing part are implanted in a jawbone, and
wherein the length of the implantation torque increasing part in the central axis direction is in the range of 0.1 mm to 1.0 mm inclusive.

2. The dental implant according to claim 1, wherein the implantation torque increasing part is configured such that an implantation torque required to implant the implantation torque increasing part into the jawbone is greater than an implantation torque required to implant, among the plurality of threading parts, the threading part that is adjacent to the implantation torque increasing part into the jawbone.

3. The dental implant according to claim 1, wherein the length, along the central axis direction, of an area of the male threading part in which the tops of the thread crests are located on the common straight line is in the range of 2.0 mm to 4.0 mm inclusive.

4. The dental implant according to claim 1, wherein the length, along the central axis direction, of an area of the male threading part in which the tops of the thread crests are located on the common straight line is in the range of 3.2 mm to 4.0 mm inclusive.

5. The dental implant according to claim 1, wherein the length of the implantation torque increasing part in the central axis direction is in the range of 0.2 mm to 0.5 mm inclusive.

6. The dental implant according to claim 1, wherein an angle that the common straight line forms with the central axis is in the range of 0.5 degrees to 8 degrees inclusive.

7. The dental implant according to claim 1, wherein an angle that the common straight line forms with the central axis is in the range of 1 degree to 4 degrees inclusive.

8. The dental implant according to claim 1, wherein the length of the lead that is common to the plurality of threading parts in the central axis direction is in the range of 0.5 mm to 2.4 mm inclusive.

9. The dental implant according to claim 1, wherein the length of the lead that is common to the plurality of threading parts in the central axis direction is in the range of 0.8 mm to 1.5 mm inclusive.

10. The dental implant according to claim 1, wherein the pitches of the plurality of threading parts are expressed by an integer ratio.

11. The dental implant according to claim 1, wherein the threading part that is arranged most toward the tip side among the plurality of threading parts multiple-start thread.

12. The dental implant according to claim 1, wherein a tip portion of the male threading part is formed on a tapered face whose cone angle is greater than that of another portion of the male threading part.

13. The dental implant according to claim 1, comprising a tap groove having a self-tapping function at the tip or the vicinity thereof.

14. A method of implanting the dental implant of claim 1 into a jawbone having a cortical bone component, comprising:

placing the dental implant in a bone hole defined in the jawbone and extending through the cortical bone component;

applying a turning force to the dental implant so that the dental implant is embedded into the jawbone with the male threading part engaging the jawbone, with the threading part that is adjacent to the implantation torque increasing part along the central axis direction engaging the cortical bone component; and stopping the application of the turning force after sensing an increase in the turning force required due to the implantation torque increasing part coming into engagement with and being embedded in the cortical bone.

15. The method according to claim 14, wherein the implantation torque increasing part is embedded entirely in the cortical bone when the application of the torque is stopped.

* * * * *